(12) United States Patent  
Ghosh et al.

(10) Patent No.: US 11,556,809 B2  
(45) Date of Patent: Jan. 17, 2023

(54) BRAIN ACTIVITY PREDICTION

(71) Applicants: UNIVERSITAT ZURICH, Zurich (CH); UNIVERSITY OF FRIBOURG, Fribourg (CH)

(72) Inventors: Arko Ghosh, Winterthur (CH); Eric Rouillier, Fribourg (CH); Magali Chytiris, Sales (CH); Myriam Balerna, Lamone (CH); Anne-Dominique Gindrat, Gottingen (CH)

( * ) Notice: Subject to any disclaimer, the term of this patent is extended or adjusted under 35 U.S.C. 154(b) by 1278 days.

(21) Appl. No.: 15/535,535

(22) PCT Filed: Dec. 14, 2015

(86) PCT No.: PCT/EP2015/079619  
§ 371 (c)(1),  
(2) Date: Jun. 13, 2017

(87) PCT Pub. No.: WO2016/096743  
PCT Pub. Date: Jun. 23, 2016

(65) Prior Publication Data  
US 2017/0351958 A1     Dec. 7, 2017

(30) Foreign Application Priority Data  
Dec. 14, 2014   (EP) .................................... 14197841

(51) Int. Cl.  
*G06N 5/04* (2006.01)  
*A61B 5/00* (2006.01)  
(Continued)

(52) U.S. Cl.  
CPC ............... *G06N 5/04* (2013.01); *A61B 5/377* (2021.01); *A61B 5/7275* (2013.01);  
(Continued)

(58) Field of Classification Search  
CPC .......... G06N 7/04; G06N 7/043; G06N 5/048; G06N 20/00; G05B 13/0275  
(Continued)

(56) References Cited

U.S. PATENT DOCUMENTS 9,983,670 B2 *   5/2018   Coleman ................. G06F 3/015  
2005/0007091 A1 *   1/2005   Makeig ................... A61B 5/374  
                                                                    324/76.13  
(Continued)

OTHER PUBLICATIONS

D'Mello et al.—"Affective Computing and Intelligent Interaction"—2011—https://link.springer.com/book/10.1007/978-3-642-24571-8?page=1#toc (Year: 2011).*

(Continued)

*Primary Examiner* — Viker A Lamardo  
(74) *Attorney, Agent, or Firm* — JMB Davis Ben-David

(57) ABSTRACT

A method for estimating a brain activity response following a stimulus of a person comprises the steps: providing a usage data set of the person from a personal device used by said person, wherein at least one usage attribute is associated to said usage data set, wherein attribute data is associated to each of the at least one usage attribute, providing a computational inference model, generated from a plurality of brain activity data sets and a plurality of usage data sets, wherein each brain activity data set comprises data derived from a brain activity response following a sensory stimulus, submitting the attribute data of each of the at least one usage attributes to said computational inference model, estimating a brain activity response following a sensory stimulus of said person by evaluating said computational inference model for the submitted attribute data. The method is useful to determine, for example the influence of intensive touch pad usage (of a smartphone) on somatosensory evoked potentials.

16 Claims, 24 Drawing Sheets

(51) Int. Cl.
G16H 50/20 (2018.01)
G16H 50/30 (2018.01)
G16H 40/67 (2018.01)
A61B 5/377 (2021.01)

(52) U.S. Cl.
CPC ........... *A61B 5/7278* (2013.01); *G16H 40/67* (2018.01); *G16H 50/20* (2018.01); *G16H 50/30* (2018.01)

(58) Field of Classification Search
USPC .......................................................... 706/1
See application file for complete search history.

(56) References Cited

U.S. PATENT DOCUMENTS

| | | | |
|---|---|---|---|
| 2012/0330178 A1 | 12/2012 | Kraft et al. | |
| 2014/0171757 A1* | 6/2014 | Kawato | A61B 5/377 600/301 |
| 2014/0228701 A1* | 8/2014 | Chizeck | G06F 21/6254 600/544 |
| 2014/0278220 A1* | 9/2014 | Yuen | A61B 5/02427 702/150 |
| 2014/0316230 A1* | 10/2014 | Denison | A61B 5/165 600/383 |
| 2016/0103487 A1* | 4/2016 | Crawford | A61B 5/377 600/544 |

OTHER PUBLICATIONS

Montjoye et al.—"Predicting Personality Using Novel Mobile Phone-Based Metrics"—2013—https://link.springer.com/chapter/10.1007%2F978-3-642-37210-0_6 (Year: 2013).*
Elbert, T., Pantev, C., Wienbruch, C., Rockstroh, B. & Taub, E. "Increased cortical representation of the fingers of the left hand in string players". Science 270, 305-307 (1995).
Hamilton, R. H. & Pascual-Leone, A. "Cortical plasticity associated with Braille learning". Trends Cogn. Sci. 2, 168-174 (1998).
Munte, T. F., Altenmuller, E. & Jancke, L. "The musicians brain as a model of neuroplasticity". Nat. Rev. Neurosci. 3, 473-478 (2002).
Kleber, B., Veit, R., Birbaumer, N., Gruzelier, J. & Lotze, M. "The brain of Opera Singers: Experience-Dependent Changes in Functional Activetion". Cereb. Cortex 20, 1144-1152 (2010).
Yarrow, K., Brown, P. & Krakauer, J. W. "Inside the brain of an elite athlete: the neural processes that support high achievement in sports". Nan. Rev. Neurosci. 10, 585-596 (2009).
Gindrat, A.-D., Chytiris, M., Balerna, M., Rouiller, E. M. & Ghosh, A. "Use-dependent cortical processing from fingertips in touch-screen phone users". Curr. Biol. 25, 109-116 (2015).
Vazquez, A. et al. "Modeling bursts and heavy tails in human dynamics". Phys. Rev. E 73, 036127 (2006).
Barabasi A.-L. "The origin of bursts and heavy tails in human dynamics". Nature 435, 207-211 (2005).
Oliveira, J. G. & Barabasi, A-L. "Human dymanics: Darwin and Einstein correspondence patterns". Nature 437, 1251-1251 (2005).
Jiang, Z.-Q. et al. "Calling patterns in human communication dynamics". Proc. Natl. Acad. Sci. U. S. A. 110, 1600-1605 (2013).
Oliveira, J. G. & Vazquez, A. "Impact of interactions on human dynamics". Phys. Stat. Mech. Its Appl. 338, 187-192 (2009).
Collignon, O. & De Volder, A. G. "Further evidence that congenitally blind participants react faster to auditory and tactile spatial targets". at <http://www.researchgate.net/profile/Anne_De_Volder/publication/40755921_Further_Evidence_That_Congenitally_Blind_Participants_React_Faster_to_Auditory_and_Tactile_Spacial_Targets/links/02e7e53901b3c9aaea000000.pdf>.
Spengler, F. et al. "Learning transfer and neuronal plasticity in humans trained in tactile discrimination". Neurosci. Lett. 232, 151-154 (1997).

Donovan, J. J. & Radosevich, D. J. "A meta-analytic review of the distribution of practice effect: Now you see it, now you don't".J App Psych 84:795-805 (1999).
Franklin, J. C. &Brozek, J. "The relation between distribution of practice and learning efficiency in psychomotor performance". J Exp. Psychol. 37, 16-24 (1947).
Whitley, J. D. "Effects of practice distribution on learning a fine motor task". Res. Q. Am. Assoc. Health Phys. Educ. Recreat. 41, 576-583 (1970).
Lee, T. D. & Genovese, E. D. "Distribution of practice in motor skill acquisition: Different effects for discrete and continuous tasks". Res. Q. Exerc. Sport 60, 59-65 (1989).
Ulrich, R., Rinkenauer, G. & Miller, J. "Effects of stimulus duration and intensity on simple reaction time and response force". at <http://e.guigon.free.fr/rsc/article/UlrichEtAl98a.pdf>.
Wenar, C. "Reaction time as a function of manifest anxiety and stimulus intensity". J. Abnorm. Soc. Psychol. 49, 335-340 (1954).
Tamm, L. et al. "Reaction time variability in ADHD: A review". Neurotherapeutics 9, 500-508 (2012).
Huber, R. et al. "Arm immobilization causes cortical plastic changes and locally decreases slow wave activity". Nat. Neurosci. 9, 1169-1176 (2006).
Allison, T., McCarthy, G. &Wood, C. C. "The relationship between human long-latency somatosensory evoked potentials recorded from the cortical surface and from the scalp". Electroencephalogr. Clin. Neurophysiol. Potentials sect. 84, 301-314 (1992).
Inui, K., Wang, X., Tamura, Y., Kaneoke, Y. & Kagiki, R. "Serial processing in the human somatosensory system". Cereb. Cortex 14, 851-857 (2004).
Romo, R., Hernandez, A., Zainos, A., Lemus, L. & Brody, C. D. "Neuronal correlates of decision-making in secondary somatosensory cortex". Nat. Neurosci. 5, 1217-1225 (2002).
Del Gratta, C et al. "Topographic organization of the human primary and secondary somatosensory cortices: Comparison of fMRI and MEG findings". NeuroImage 17, 1373-1383 (2002).
Grill-Spector, K., Henson, R. & Martin, A. "Repetition and the brain:Neural models of stimulus-specific effects" Trends Cogn. Sci. 10, 14-23 (2006).
Rioult-Pedotti, M.-S., Friedman, D., Hess, G. & Donoghue, J. P. "Strengthening of horizontal cortical connections following skill learning". Nat. Neurosci. 1, 231 (1998).
Hsieh, C.-L., Shima, F., Tobimatsu, S., Sun, S.-J. & Kato, M. "The interaction of the somatosensory evoked potentials to simultaneous finger stimuli in the human central nervous system". A study using direct recordings. Electroencephalogr. Clin. Neurophysiol. Potentials Sect. 96, 135-142 (1995).
Gandevia, S. C., Burke, D. & McKeon, B. B. "Convergence in the somatosensory pathway between cutaneous afferents from the index and middle fingers in man". Exp. Brain Res. 50, 415-425 (1983).
Fross, N., Jousmaki, V. & Hari, R. "Interaction between afferent input from fingers in human somatosensory cortex". Brain Res. 685, 68-76 (1995).
Oldfield, R. C. "The assessment and analysis of handedness: The Edinburgh inventory". Neuropsychologia 9, 97-113 (1971).
Clauset, A., Shalizi, C. R. & Newman, M. E. "Power-law distributions in empirical data". SIAM Rev. 51, 661-703 (2009).
Lacouture, Y. &Cousineau, D. "How to use MATLAB to fit the ex-Gaussian and other probability functions to a distribution of response times". Tutor. Quant. Methods Psychol. 4, 35-45 (2008).
Chaumon, M., Bishop, D. V. M. & Busch, N. A. "A practical guide to the selection of independent components of the electroencephalogram for artifact correction". J. Neurosci. Methods doi:10.1016/jneumeth.2015.02.025.
Pernet, C. R., Chauveau, N., Gaspar, C. & Rousselet, G. A. "LIMO EEG: A toolbox for heirarchical linear modelibg of electroencephalographic data". Comput. Intell. Neurosci. Mar. 2011, (2011).
Andrew D et al: "Somatosensory evoked potentials show plastic changes following a novel motor training task with the thumb", Clinical Neurophysiology, vol. 126, No. 3, Jun. 5, 2014, pp. 575-580.
Gindrat Anne-Dominique et al: "Use-Dependent Cortical Processing from Fingertips in Touchscreen Phone Users", Current Biology, vol. 25, No. 1, Jan. 5, 2015, pp. 109-116.

(56) References Cited

OTHER PUBLICATIONS

T. Elbert et al: "Increased Cortical Representation of the Fingers of the Left Hand in String Players", Science, vol. 270, No. 5234, Oct. 13, 1995, pp. 305-307.
Berolo S et al: "Musculoskeletal symptoms among mobile handheld device users and their relationship to device use: A preliminary study in a Canadian university population", Applied Ergonomics, Butterworth Scientific Ltd, Guildford, GB, vol. 42, No. 2, Jan. 1, 2011, pp. 371-378.
Sylvain Senecal et al: "Mouse vs. Touch Screen as Input Device: Does it Influence Memory Retrieval?", Thirty Fourth International Converence on Information Systems, Dec. 1, 2013.

\* cited by examiner

Method 2. – Real time data: individual user analysis

Application 1. – Using population model

Application 2. – Using individual model

Application 4. – Using population model to infer individual brain activity and market products g Mean event related potential (n = 54)

-0.6          0.6 µV 70 ms     110 ms

Multiple regression $R^2$ (p<0.05)

0.0          0.3

BRAIN ACTIVITY PREDICTION

CROSS-REFERENCE TO RELATED APPLICATIONS

This is the U.S. National Stage of International Application No. PCT/EP2015/079619 filed Dec. 14, 2015, which was published in English under PCT Article 21(2), and which in turn claims the benefit of European Patent Application No. 14197841.1 filed Dec. 14, 2014.

The invention relates to a method for predicting the brain activity response following a stimulus of a person according to claim 1 and a computer program according to claim 15.

Cortical activity allotted to the tactile receptors on fingertips conforms to skillful use of the hand. For instance, in musical string players the somatosensory cortical activity in response to touch on the little fingertip is larger than in control subjects. Such plasticity of the fingertip sensory representation is not limited to extraordinary skills and occurs in monkeys trained to repetitively grasp and release a handle as well.

Many personal devices such as for example touchscreen phones require repetitive finger movements as well and therefore impact the cortical activity particularly the somatosensory brain activity response following a somatosensory stimulus, such as a tactile stimulus of the finger tip.

The state of the art knows methods used to predict brain signals, such as in using prior brain signals to detect seizures and methods using brain signal history to train brain-machine interfaces.

However, it is not possible to estimate the cortical activity following a somatosensory stimulus, by solely taking into account personal device usage in the past or to account for the influence of the usage of such a personal device on the cortical activity.

The problem according to the invention is to provide a method that estimates the cortical activity response following a somatosensory stimulus based on the past usage of a personal device.

According to claim 1, a method for estimating a brain activity response following a stimulus of a person comprises the steps:
  providing a usage data set of the person from a personal device used by said person, wherein at least one usage attribute particularly related to the use of the personal device is associated to said usage data set, wherein attribute data is associated to each of the at least on usage attribute,
  providing a computational inference model, which relates the attribute data to the brain activity response, wherein said computational inference model is generated from a plurality of brain activity data sets and a plurality of usage data sets, particularly acquired prior the acquisition of the plurality of brain data sets, wherein each brain activity data set comprises data derived from a brain activity response to a sensory, particularly tactile stimulus, particularly of a finger, particularly of the thumb tip,
  submitting the attribute data of each of the at least one usage attributes to said computational inference model,
  estimating a brain activity response following a sensory, particularly tactile stimulus of said person by evaluating said computational inference model for the submitted attribute data.

Providing usage data is particularly facilitated by recording, storing and/or measuring said usage data on a personal device with a subsequent transmission of said usage data. Furthermore said usage data particularly is the attribute data of the at least one usage attribute. Usage data particularly refers to any kind of data that is correlated to a usage of the personal device, such as for example a temporal course of a battery log of the personal device. Said personal device is for example a smart phone comprising a touchscreen or a device specifically designed for recording such, particularly somatosensory interactions of a person with said device.

A usage attribute particularly is a feature associated or exhibited by the usage data, such as for example the use of the personal device per hour. An attribute data is particularly a scalar or a vector representing said usage attribute.

A computational inference model is particularly a function or relation that particularly relates at least one input variable, such as for example the attribute data, to a brain activity response. Such a computational inference model is particularly defined through particularly pre-calculated event-related coefficients that are particularly represented as a heat map.

Submitting the attribute data to the computational inference model can be facilitated by entering said attribute data in the computational inference model, wherein said computational inference model is providing corresponding input opportunities.

The estimation of the brain activity response is particularly done by calculating a brain activity value for a plurality of locations in the brain, wherein such value particularly represents an event-related potential (ERP). ERPs are quantities that are particularly recorded by a scalp electrode of an electroencephalography recording device.

In contrast to the estimation the recording of the brain activity response following a stimulus of a person is particularly performed by measure an event-related potential that in turn has its origin in an event-related dipole field around the contralateral cortex.

In a preferred embodiment the estimation of the brain response is done by estimating an event-related coefficient particularly for a plurality of electrode locations on the scalp. The term brain activity is particularly referring to said measurable dipole field around the contralateral cortex, particularly via the event-related potential (ERP). The term brain activity data set particularly refers to data that comprise a measure of said dipole field.

In a preferred embodiment of the invention the computational inference model is generated by conducting the following steps:
  providing a plurality of brain activity data sets that particularly comprise spatiotemporal signals recorded from the brain, wherein said signals are particularly evoked by the dipole field around the contralateral cortex, and particularly acquired by at least one scalp electrode,
  providing a plurality of said usage data sets, from the person from which the plurality of the brain activity data sets have been acquired from or from persons of which the plurality of brain data sets have been acquired from, wherein said usage data sets are particularly acquired prior the acquisition of the plurality of brain activity data set,
  estimating for each usage data set of the plurality of usage data sets the attribute data associated to the at least one usage attribute, yielding for each usage attribute a plurality of attribute data,
  submitting the plurality of brain activity data sets and the plurality of the attribute data to a regression analysis, particularly a multiple linear regression analysis or a machine learning algorithm, wherein said regression analysis determines said computational inference model.

In the field of regression analysis, the brain activity data sets are termed the "dependent variables", the usage data sets are termed the "independent variables" and the computational inference model is termed the "function" relating the independent and dependent variables to each other, particularly via so called "unknown parameters", e.g. event-related coefficients. A regression analysis in this context also refers to machine learning algorithms and methods. As regression analysis and machine learning methods are overlapping fields, both are suitable for estimating and generating the computational inference model. In mathematics particularly in the field of regression analysis, the estimation of such a relating function, using statistics on dependent and independent variables is well established.

The spatiotemporal signals, particularly the event-related potentials, are particularly recorded with an EEG, a functional magnet resonance imaging method (fMRI), a positron emission tomography method (PET), a functional near-infrared spectroscopy (fNIRS) method and/or an electrocorticography (ECoG) method. Therefore the signals are particularly recorded in a distributed manner over a section or a volume of the brain or scalp, leading to a potentially spatially variable signal. Furthermore said signals are particularly of transient nature and therefore a temporally varying quantity. The time scale of said temporal variations is particularly on the millisecond timescale.

In another embodiment of the invention the regression analysis is a multiple linear regression analysis wherein said regression analysis is designed such that an event-related coefficient for each of the at least one usage attribute is determined, wherein the computational model is particularly a function relating the attribute data associated to a usage attribute by means of the event-related coefficients to a brain activity response following a sensory, particularly tactile stimulus, particularly of a finger, particularly of the thumb tip.

As described above, the linear regression analysis particularly yields the so-called unknown parameters which in the context of the present invention are particularly termed event-related coefficients. Once the event-related coefficients have been determined, submitting attribute data to the computational inference model will particularly yield a spatiotemporal map of expected brain response signals. The computational inference model is particularly fully described by the event-related coefficients. In the present invention said event-related coefficients are particularly functions of time and space, i.e. the location in the brain where the transient response signal is to be predicted/estimated.

In another embodiment according to the invention the at least one usage attribute is:
 a use per hour of the personal device by the person, particularly within the past ten days, that is particularly simply termed as 'use per hour' and wherein the attribute data particularly comprises the total power drain of the personal device per hour,
 an age at which the person first began using the personal device, particularly termed 'age of inception', and wherein the associated attribute data is the age of inception to the device,
 a time elapsed from a period of intense use of the personal device by the person to a measurement of brain activity for providing brain activity data, wherein the attribute data is a measure that comprises the time elapsed from a maximum power drain per hour,
 a moment or cumulant function of the usage data set, particularly the mean value or the variance of the power drain,
 a number of touchscreen events of the personal device per unit of time, particularly per day or per hour,
 a distribution of time intervals between touchscreen events of the personal device, and/or
 a parameter, particularly a power law exponent, of a distribution of time intervals between touchscreen events of the personal device.

Therein, the term "touchscreen event" designates a contact of a finger, particularly a thumb or an index finger, on the touchscreen of the personal device.

The term "power law distribution" describes a distribution according to a function $P(\tau)$ that is proportional to the term $\tau^{-\alpha}$, wherein $\tau$ designates the time interval between touchscreen events, and wherein $\alpha$ is the power law exponent.

In particular, it could be demonstrated that the distribution of time intervals between touchscreen events follows a power law distribution, wherein the power law exponent can be used as a measure for the priority of personal device use over all other actions in a given individual.

According to the invention it is possible to generate a computational inference model from a plurality or just one of such usage attributes/attribute data.

In another embodiment of the invention the computational inference model is a personal inference model, wherein said plurality of brain activity data sets is acquired repeatedly from a person, particularly over a range of several days, and wherein the plurality of the usage data sets is acquired from the same person, particularly within the same range of days. The personal inference model therefore is based solely on data provided by one person.

It is advantageous that in this embodiment of the invention alterations of the brain activity over time of a single person might be discovered that potentially indicate a cortical malfunction, particularly after brain surgery.

In another embodiment of the invention the computational inference model is a computational population inference model, wherein said plurality of brain activity data sets is acquired particularly repeatedly, particularly over a range of several days, from a plurality of persons, particularly 20 to 30 or more persons, and wherein the plurality of the usage data sets is acquired from the same plurality of persons particularly over a range of several days. The computational population inference model therefore is based at least partially on data provided by a plurality of persons.

This way the statistics of the computational inference model of predicting a brain response might be improved rapidly.

In another embodiment of the invention the usage data set is provided to the computational inference model comprising a temporal resolution of at least ten minutes, and wherein said usage data set is particularly acquired from a battery log, a touch screen log, a keypad log, a data exchange log and/or an accelerometer of the personal device.

The various logs exhibit advantages for evaluating the usage of the personal device. For example:
 a touchscreen data log particularly provides a spatial and temporal log of the touchscreen pixels activated by the user, particularly by using a finger,
 an accelerometer data log can determine the state of the personal device in use and body posture, a phone app log, if the personal device of a phone particularly determines the context of phone use, an app content log might be used to infer the audio, visual and tactile sensory experiences accumulated by the person, a GPS might be used determine the environmental parameters at the time of the phone use.

These kinds of logs particularly provide usage data that are suited for defining suitable usage attributes and provide suitable attribute data.

Other usage attributes might be the age, height, sex and/or the handedness of the person.

A battery log particularly refers to the history of battery charging and uncharging of a particularly battery driven personal device. A battery log is therefore particularly an indicator of device usage and is thus suited as a source of usage data. A battery log is an energy efficient and almost ubiquitous source of usage data of battery driven personal devices.

In another embodiment of the invention the usage data set is provided by a personal device comprising a body-machine interface, particularly a touch screen and/or a keypad and wherein said personal device is particularly a smart phone or a tablet computer or particularly sensors linked, particularly via a radio connection, particularly via Bluetooth or by cable to the personal device. Such sensors are for example comprised in a smartwatch, an exercise band, a headset, a head-mountable display, a heart rate monitor. Bluetooth is a wireless technology standard for exchanging data over short distances, particularly using short-wavelength UHF radio waves in the ISM band from 2.4 to 2.485 GHz.

A computer might be as well a computer-like device, comprising a microprocessor.

A tablet computer particularly comprises a touchscreen. A touchscreen comprises any kind of screen or display that is suited for a haptic interaction in order enable the person to interact with the personal device.

In another embodiment of the invention the device is used by the person on average at least five times per week and at least 15 minutes per day, such that the usage data comprises particularly enough statistics.

In another embodiment of the invention the computational inference model is a spatiotemporal scalp map or a pre-calculated look-up table, particularly comprising the same temporal resolution as the brain activity dataset.

In another embodiment of the invention each of the plurality of brain activity data sets is acquired by an electroencephalography method, a functional magnet resonance imaging method, a positron emission tomography method, a functional near-infrared spectroscopy and/or an electrocorticography method.

In another embodiment of the invention the estimated brain activity response following a sensory, particularly somatosensory, more particularly tactile stimulus of said person is displayed to the person. The advantage of this embodiment is particularly that said person receives a qualified feedback on its personal device use.

In another embodiment of the invention a value is generated, wherein said value is a function of the estimated brain activity response of said person and wherein said value furthermore is related particularly to a previously estimated value for the estimated brain activity response of said person or to an average value, of the kind of temporal or ensemble average, for the estimated brain activity response of said person or a plurality of persons.

In another embodiment of the invention the estimated brain activity response to a sensory stimulus of said person by said evaluation of said computational inference model is compared to the estimated brain activity response based on a computational inference model that has been updated with brain activity datasets that have been recorded after said first estimation.

It is advantageous to compare such estimations for example in clinical settings, when brain activity recovery or any other alteration in brain activity is to be monitored.

In another embodiment of the invention
the usage data set is generated by an interaction of the person with the personal device,
the usage data set is particularly stored on said personal device,
the attribute data is extracted from said personal device,
the attribute data is particularly stored in a usage database,
the brain activity data set is acquired, and
the brain activity data set is stored in a brain activity database.

Furthermore, the problem underlying the present invention is solved by a computer program having the features of claim 15. Said computer program comprises program code, wherein said program code prompts a computer to execute the method according to the present method, when the computer program is loaded, installed or executed on the computer.

Herein, particularly, the one way flow of the inference model is emphasized. However, in general, the model can be used both ways as they are derived from correlations. Just like one can estimate the amount of brain activity and simple sensorimotor computations from phone usage, one can also do the reverse according to a second aspect of the present invention, namely (automatically) estimate the attributes of phone use by using brain activity measures.

Particularly, according to this second aspect of the present invention a method for estimating a usage data set of a person from a personal device used by said person is provided, wherein at least one usage attribute particularly related to the use of the personal device is associated to said usage data set, and wherein attribute data is associated to each of the at least on usage attribute, wherein the method comprises the steps of:

providing a brain activity data set comprising data derived from a brain activity response of said person to a sensory, particularly tactile stimulus, particularly of a finger, particularly of the thumb tip, providing a computational inference model, which relates the brain activity data set to the attribute data of a usage data set, wherein said computational inference model is generated from a plurality of usage data sets and a plurality of brain activity data sets, and wherein each brain activity data set comprises data derived from a brain activity response to a sensory, particularly tactile stimulus, submitting the brain activity data set to said computational inference model, estimating a usage data set of said person by estimating the attribute data of at least one usage attribute by means of said computational inference model.

Further features and advantages of the invention shall be described by means of detailed descriptions of embodiments of the present invention with reference to the figures, wherein FIGS. 1.1-2 show tactile event-related potentials in touchscreen phone users and nonusers;

FIGS. 2.1-2 show inter-individual variations in thumb event-related potentials were related to touchscreen phone battery logs;

FIGS. 3.1-2 show the 'phone use per hour' usage attribute related to the index finger event related coefficient;

Figure 1:
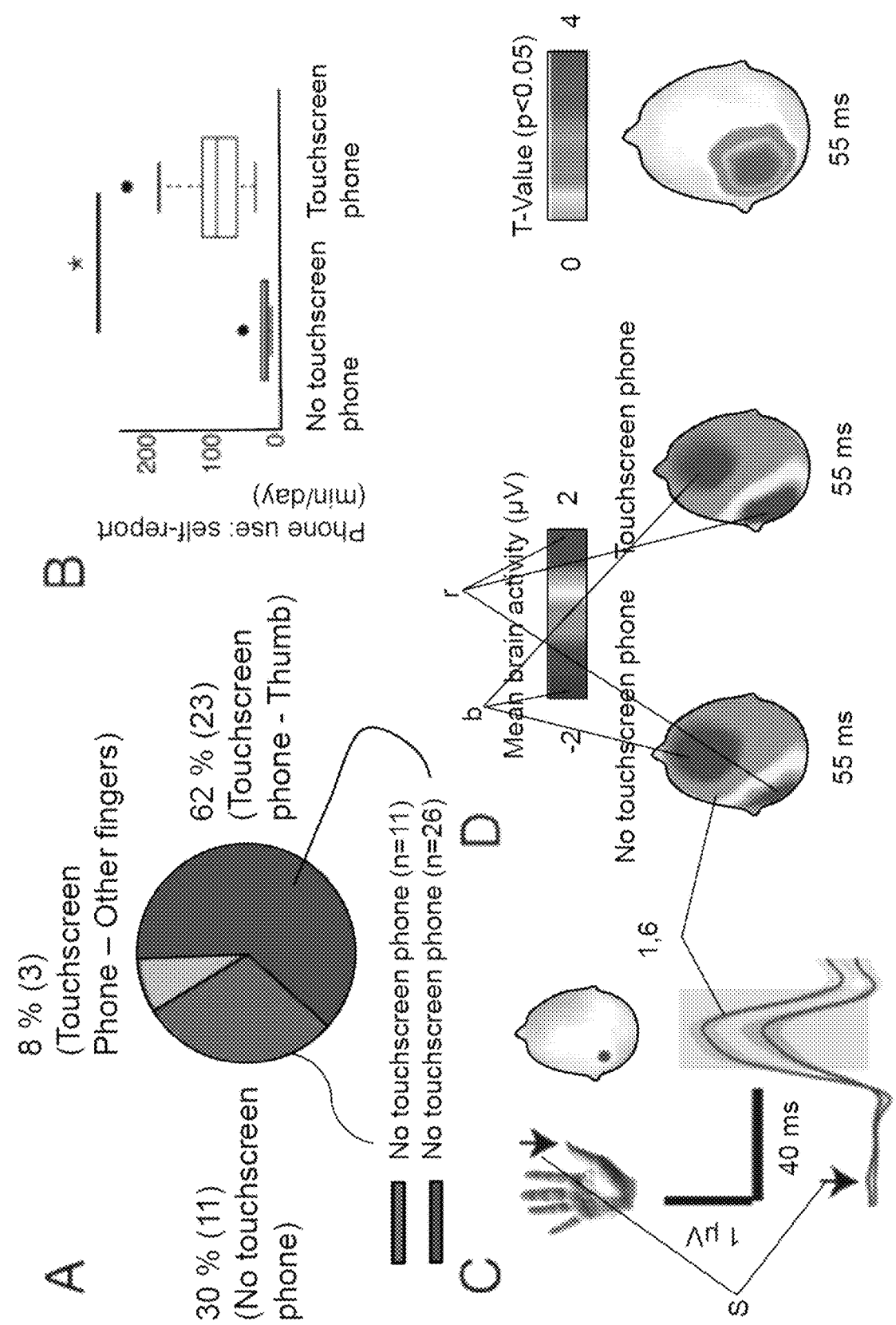
Figure 1:
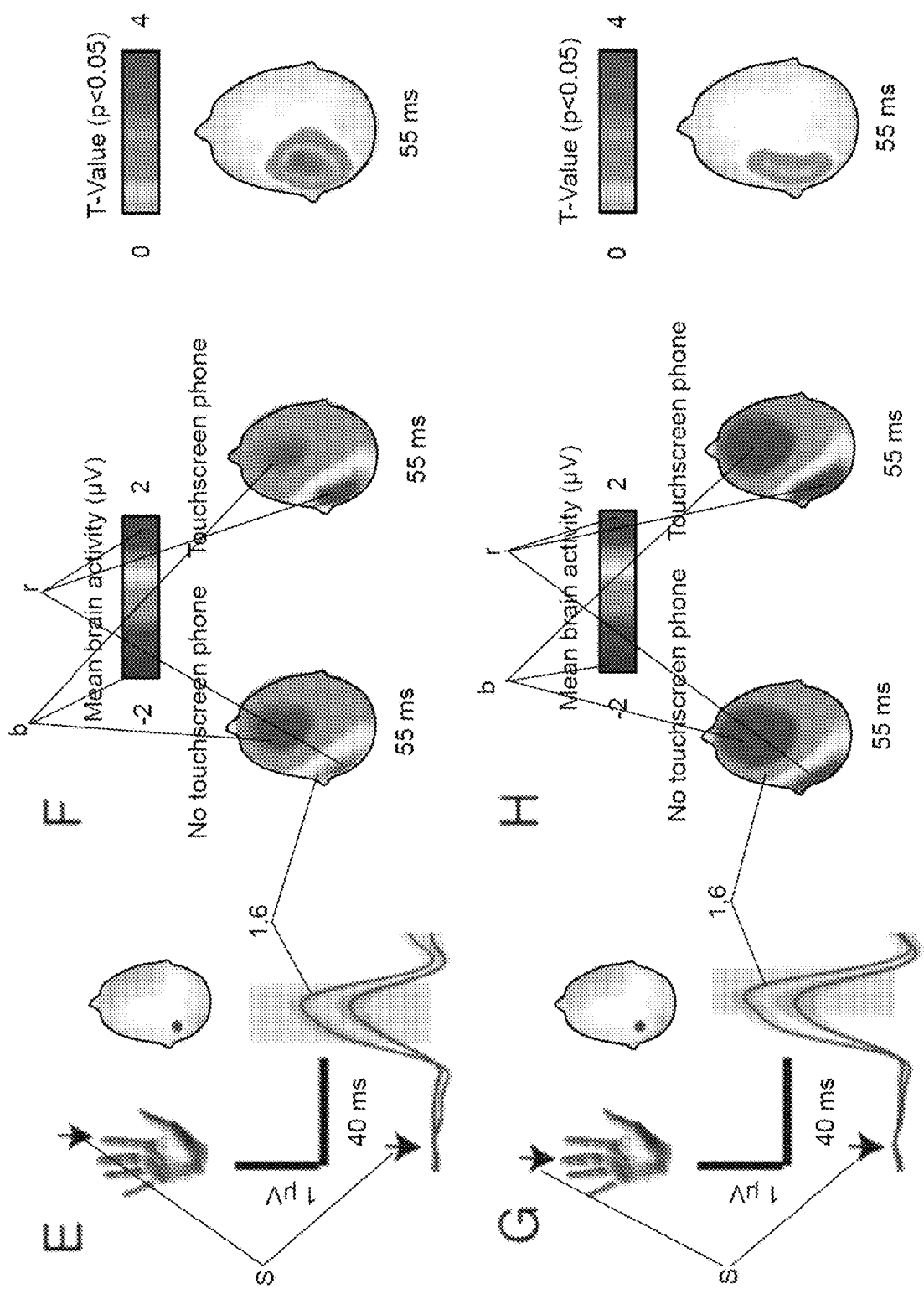
Figure 12:
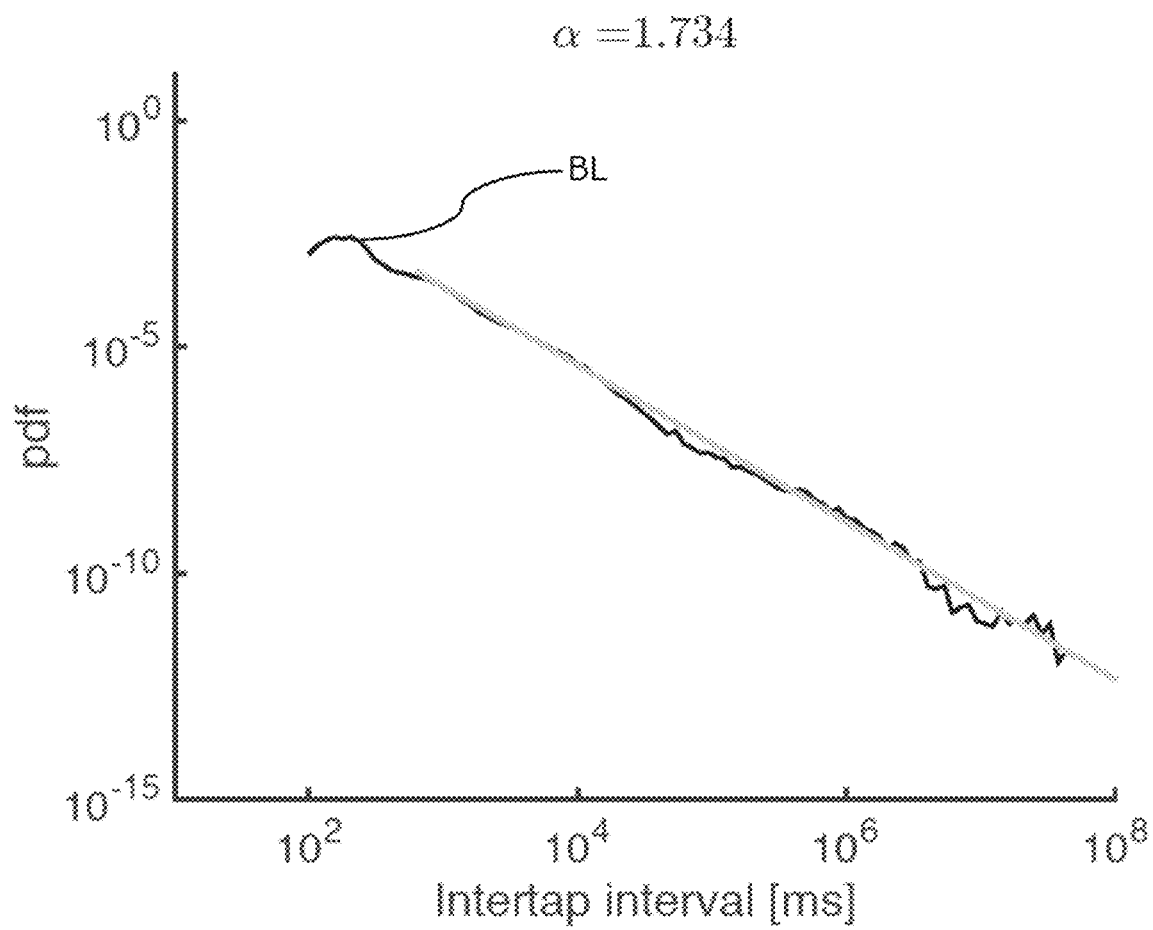
Figure 12:
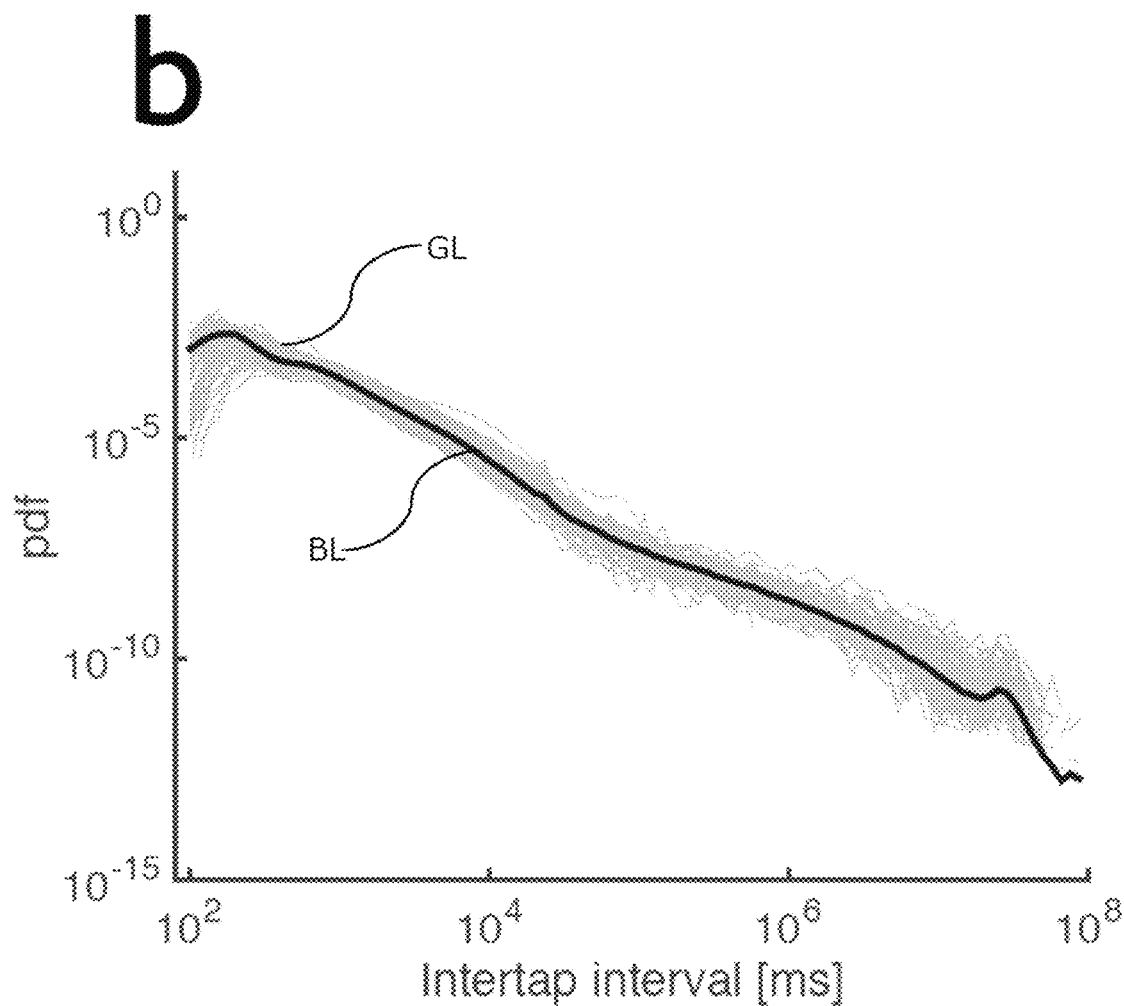
Figure 12:
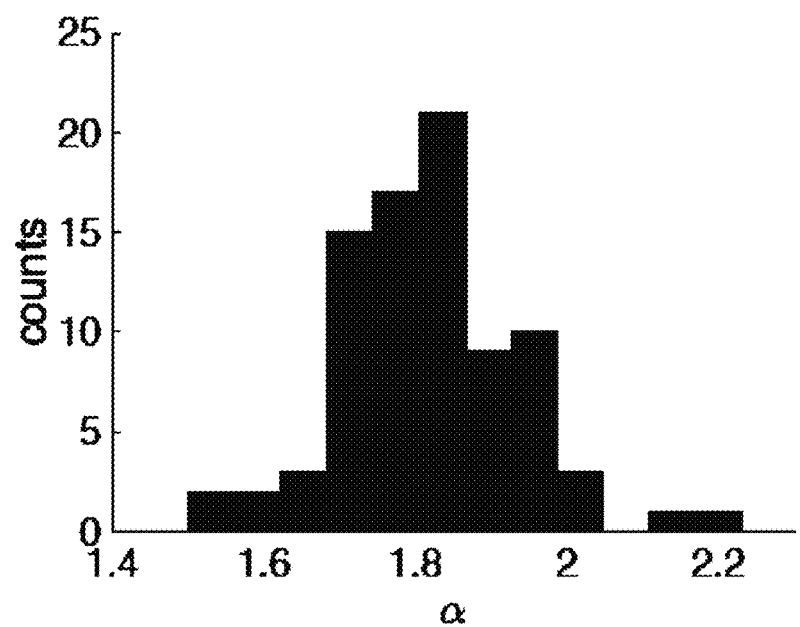
Figure 12:
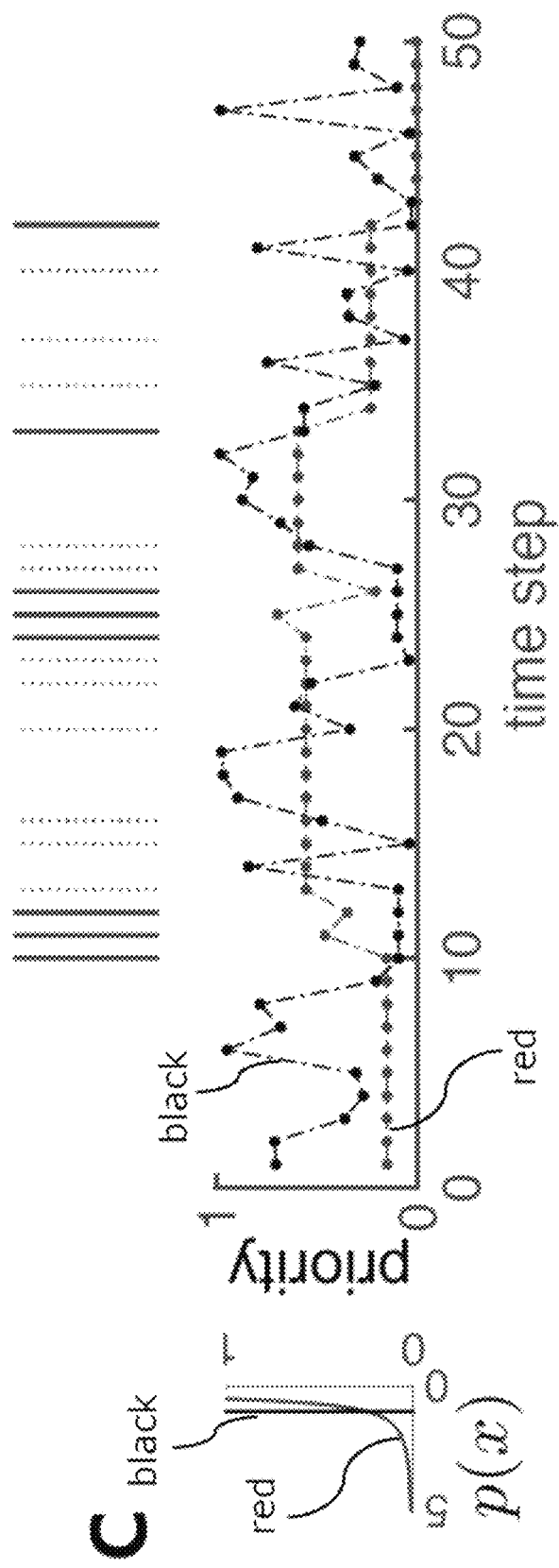
Figure 12:
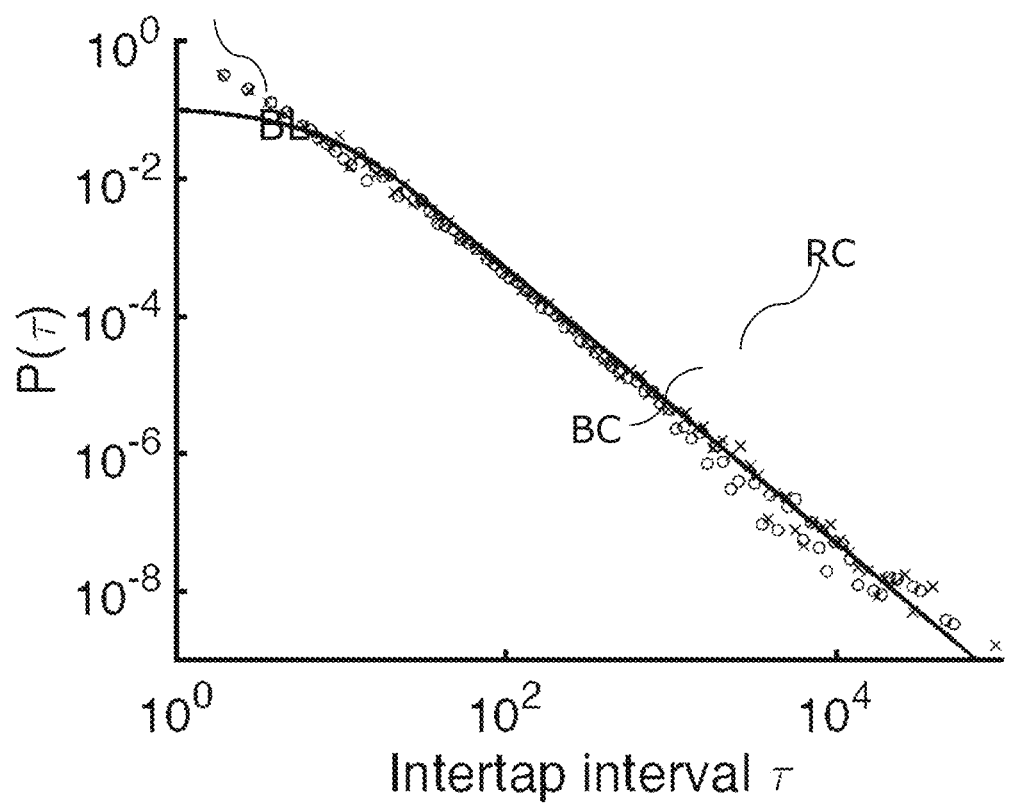
Figure 12:
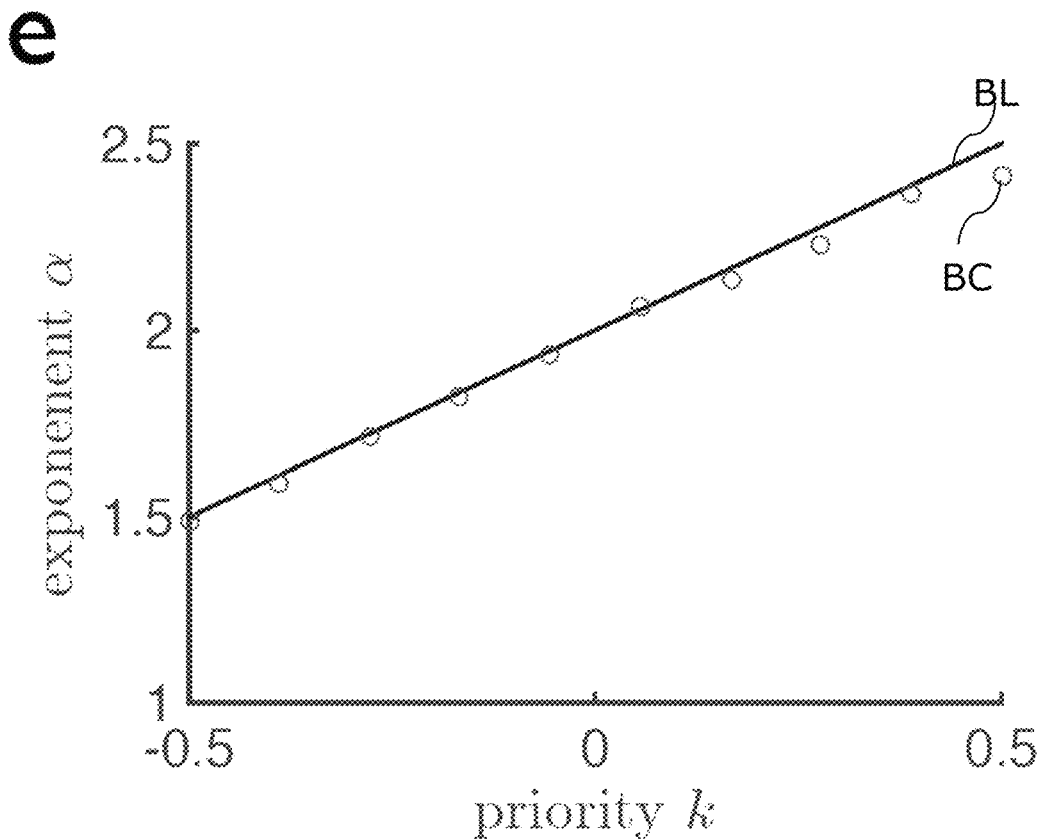
Figure 13:
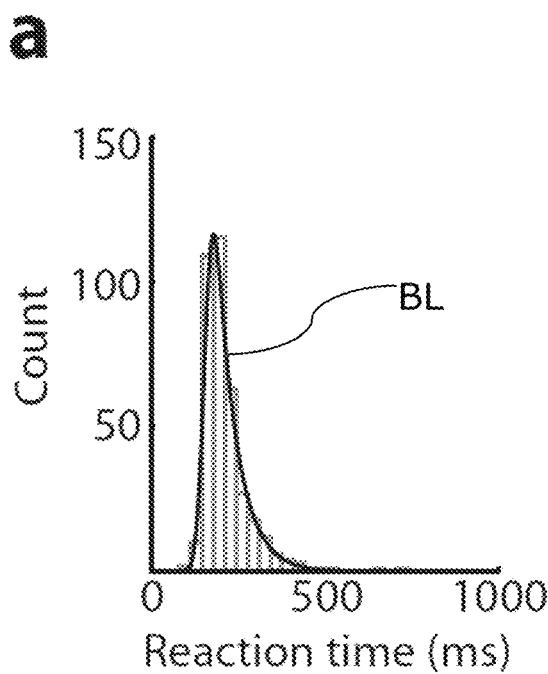
Figure 13:
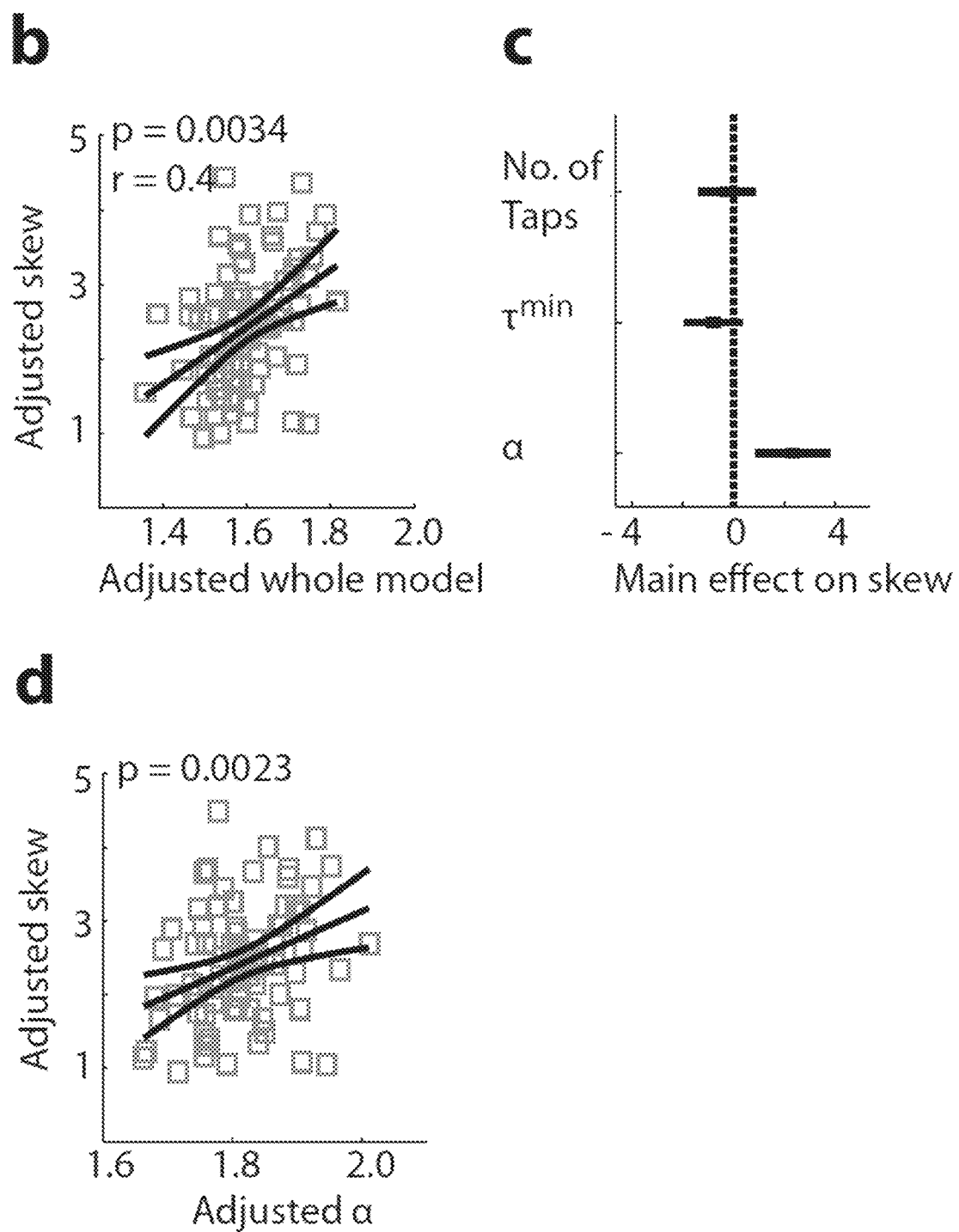
Figure 14:
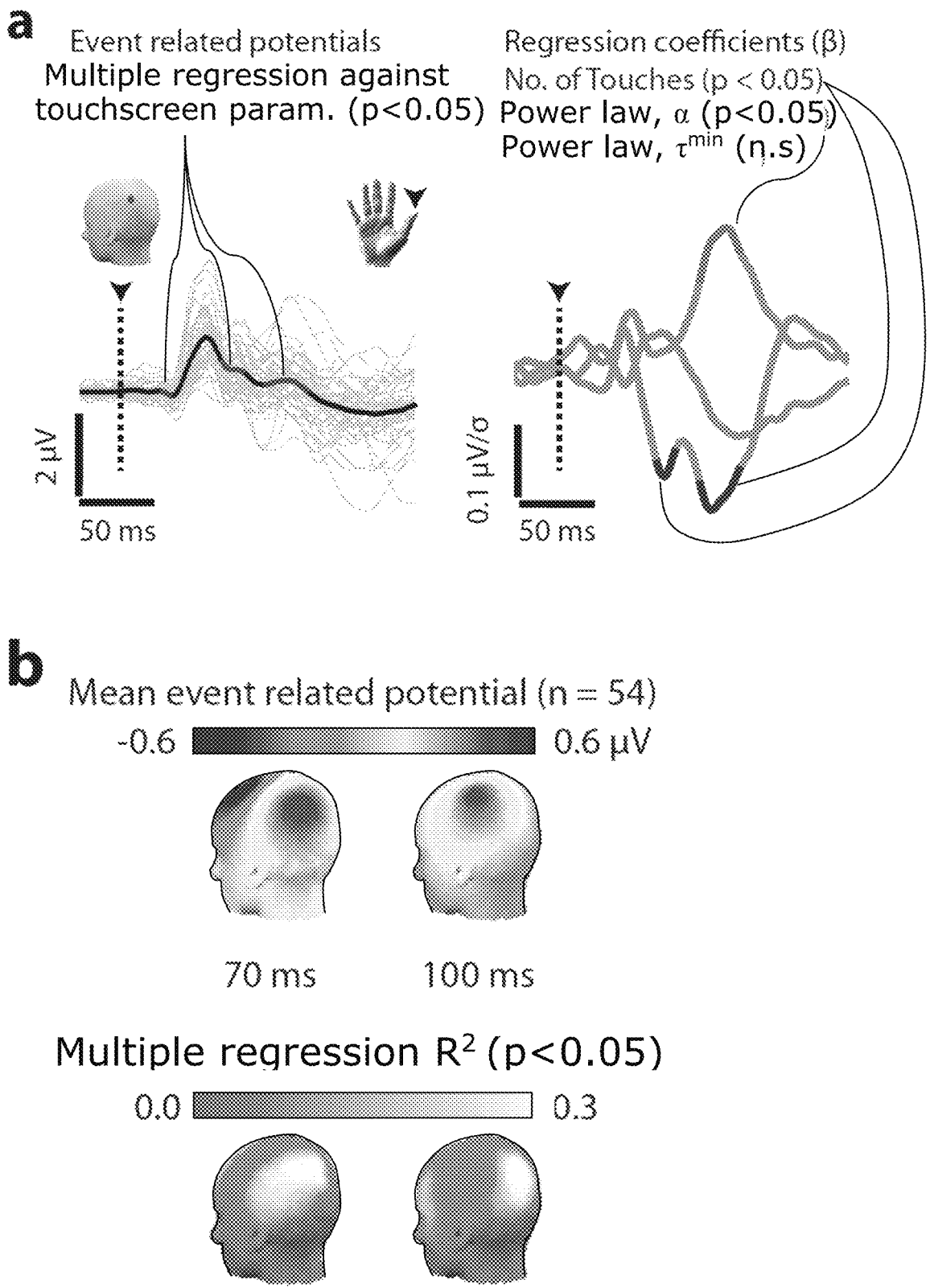
Figure 14:
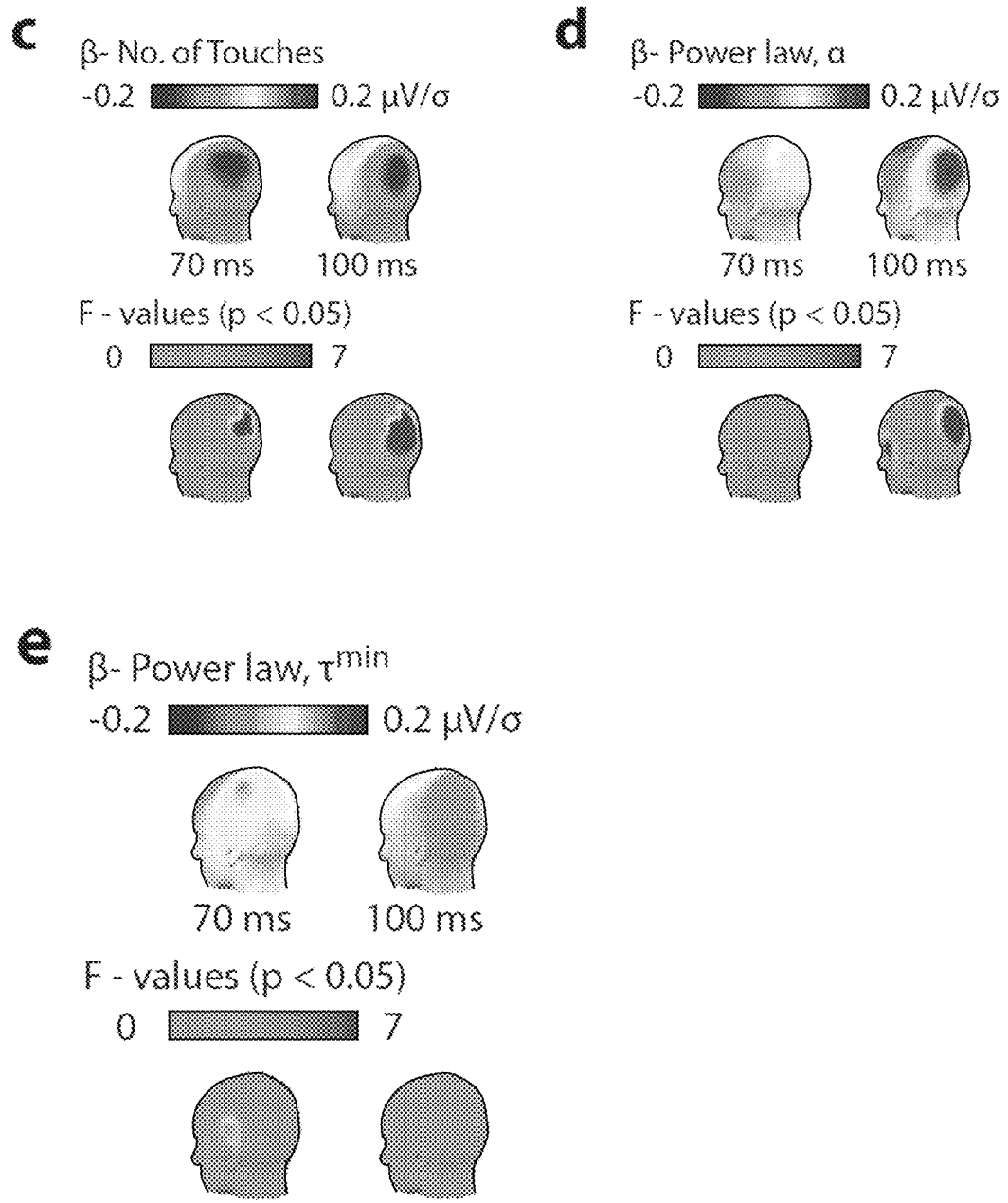
Figure 14:
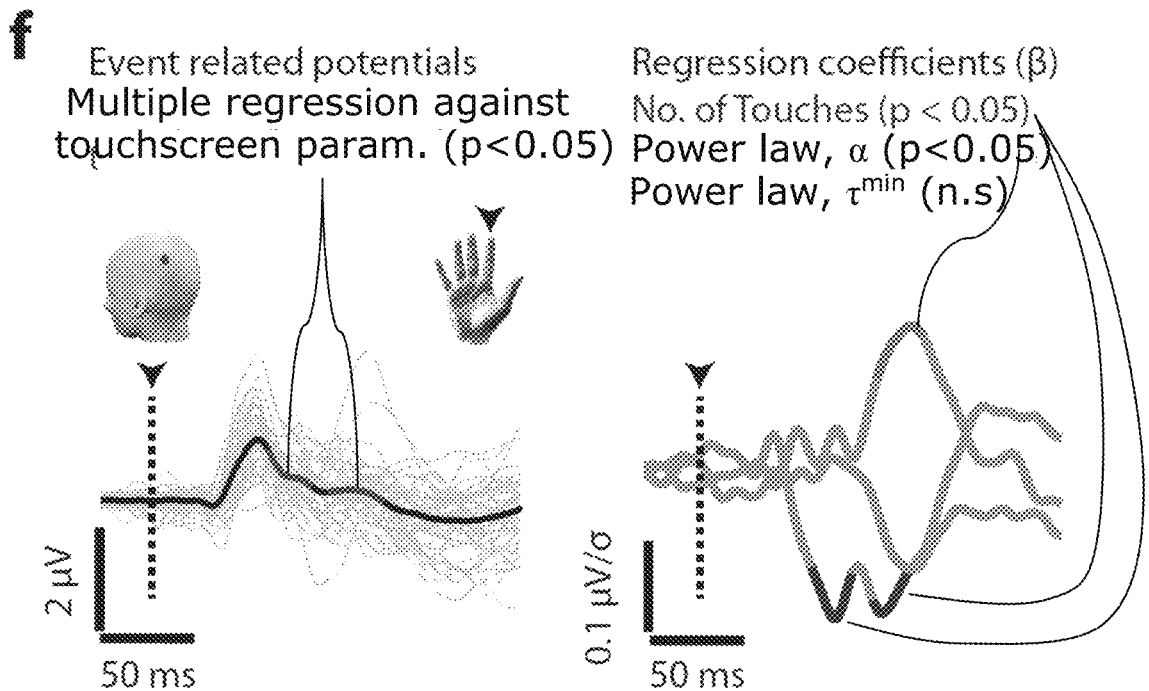
Figure 14:
Figure 14:
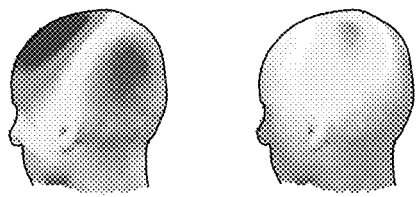
Figure 14:
Figure 14:
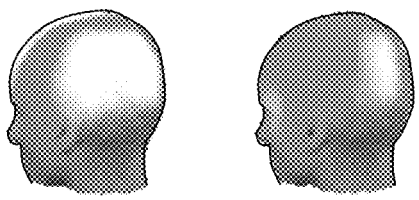
Figure 14:
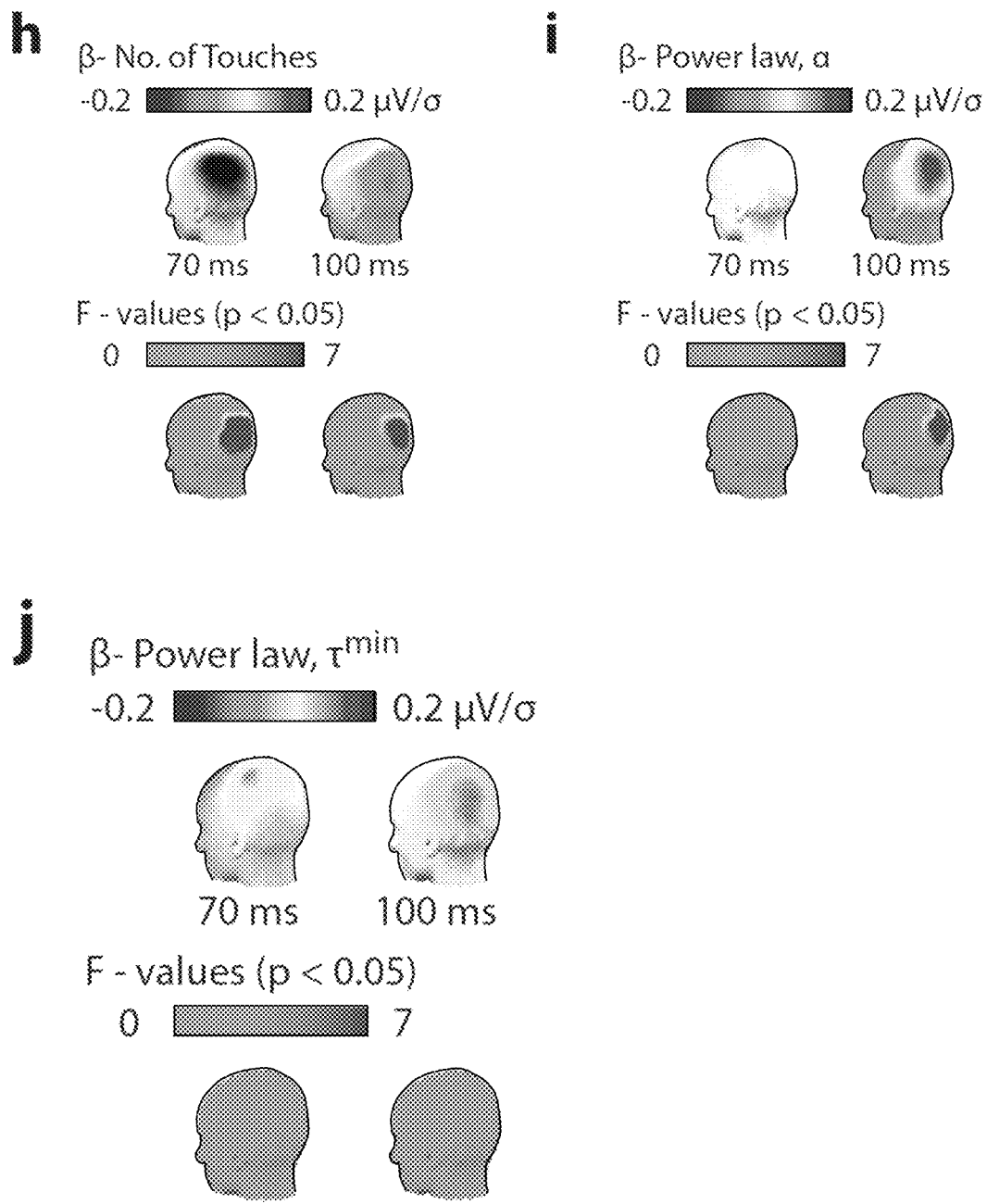

FIGS. 12.1-5 show inter-touch intervals (ITI) follow a power-law distribution;

FIGS. 13.1-2 show simple reaction times in response to tactile inputs on the thumb tip are correlated to touchscreen behavior; and FIGS. 14.1-4 show sensory evoked potentials recorded from the scalp are correlated to the touchscreen behavior FIGS. 1.1 and 1.2 show tactile event-related potentials 7 (ERPs) in touchscreen phone users and nonusers. FIG. 1.1A depicts the share of the touchscreen phone users (dark and light grey) and users of old-technology phones without touchscreen (middle grey), and most of the touchscreen users relied on their right thumb to interact with the screen (dark grey). FIG. 1.1B shows a box plot showing self-reported time spent using their mobile phone by smartphone users and nonusers. Plot description: 25th and 75th percentile box, 10th and 90th percentile whiskers. Outliers are represented by black dots. * $p<0.05$, Wilcoxon Rank Sum test.

FIG. 1.1C shows a schematic hand where the location of a tactile stimulus S is applied to the tip of a thumb of a person. The temporal onset of said stimulus S is indicated as an arrow on a graph showing the brain activity response 1 at one electrode recorded with an EEG. The particular location of the electrode that recorded said part of the brain activity data set 6 is indicated as a grey spot on the scalp representation on top of the graph. FIG. 1.1C shows two scalp maps of the brain activity data set 6 at the time 55 ms.

FIG. 1.1C particularly shows group means of the event related potentials ERPs±SEM (lighter shade) from the electrode with maximal positivity dot on the scalp map in response to the right thumb tip stimulation in touchscreen users and nonusers. Grey rectangular area depicts significant differences between both groups—$p<0.05$ and $T>1$. The small arrow above the traces points at the stimulation S onset (i.e. 0 ms). In FIG. 1.1D the corresponding scalp maps of the ERPs at 55 ms comparing the touchscreen users and non-users are depicted. The multiple comparison corrected T-value map revealed the electrodes with significant differences at 55 ms.

FIG. 1.2E and FIG. 1.2F show the same features as FIG. 1.1C and FIG. 1.1D, but with a stimulus S applied to the index finger tip of a person.

FIG. 1.2G and FIG. 1.2H show the same features as FIG. 1.1C and FIG. 1.1D, but with a stimulus S applied to the middle finger tip of a person.

Figure 2:
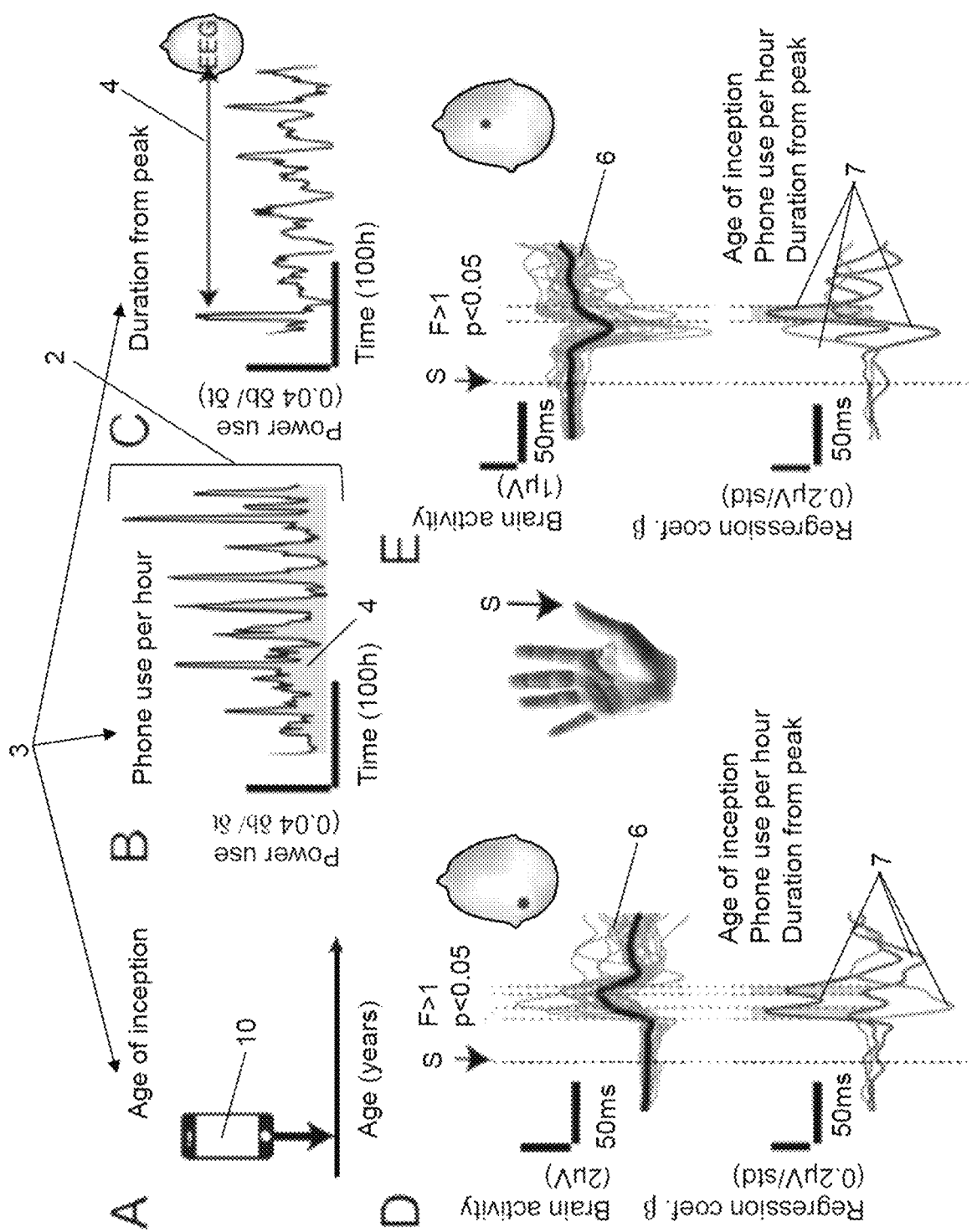
Figure 2:
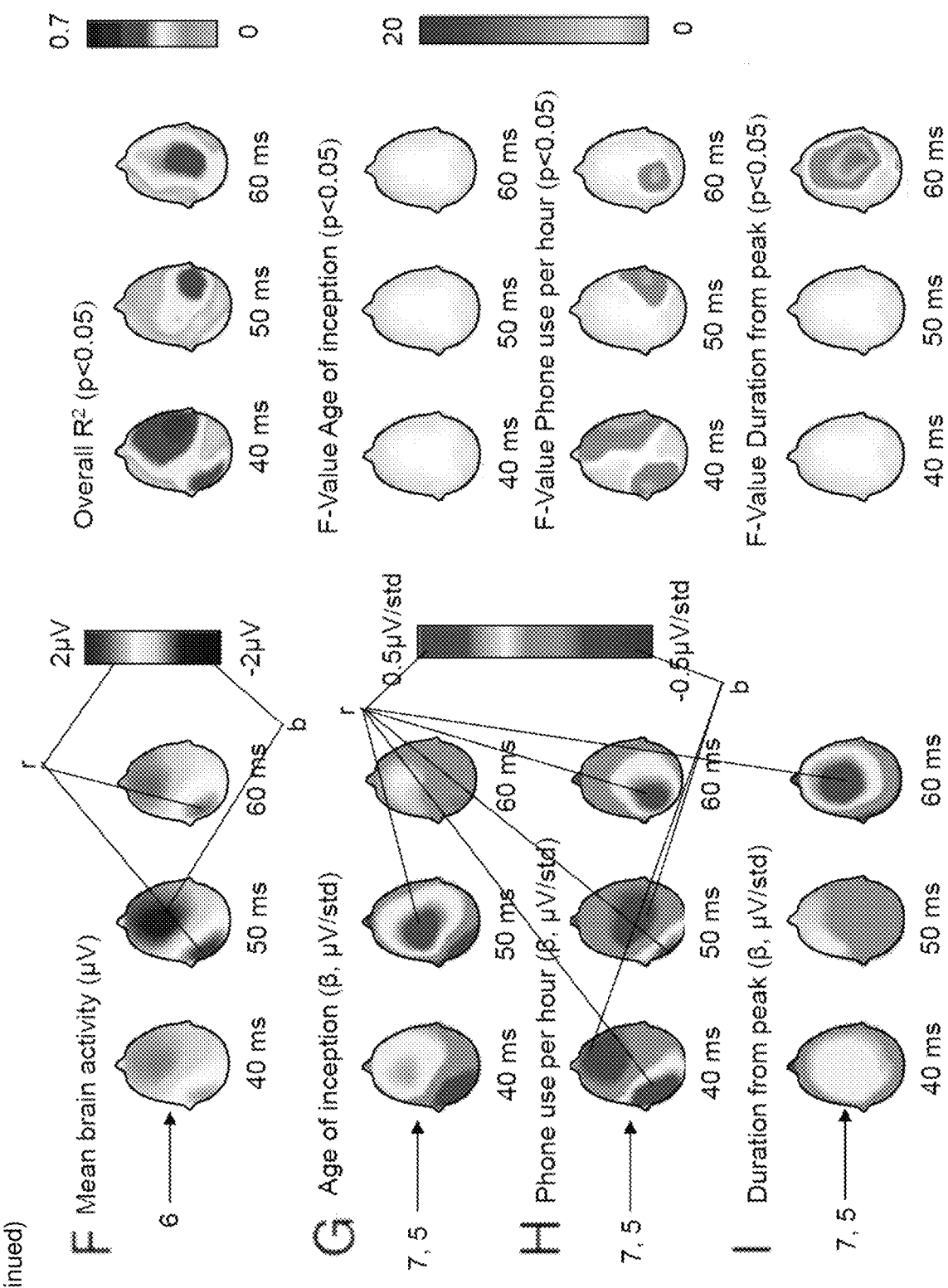

FIGS. 2.1 and 2.2 show inter-individual variations in thumb ERPs were related to touchscreen phone battery logs. FIG. 2.1A to FIG. 2.1C show three usage attributes 3. FIG. 2.1A shows the usage attribute 3 'Age of inception' of the personal device 10, comprising attribute data 4 being the year of inception of the personal device 10 to the person. The identified three particularly independent usage attributes 3 were used for a regression analysis, particularly multiple regression analysis in order to generate a computational inference model 5. FIG. 2.1A shows the usage attribute 3 'age of inception' determined from self-reports regarding the age at which the person began using a personal device 10, particularly a smartphone. FIG. 2.1B depicts the usage data 2, particularly the battery log data, from which another usage attribute 3 was extracted by determining the area under the curve in order to determine how much the personal device, particularly the smartphone was used in a 10-day period (usage attribute 3 'phone use per hour') and FIG. 2.1C depicts the 'duration from peak' of use to EEG measurement expressed as natural log of hours usage attribute 3. The three usage attributes 3, particularly the associated attribute data 4 were Z' normalized. The regression analysis of the right thumb tip ERPs, particularly the brain activity data sets 6, resulted in a time series of event-related coefficients 7 (ERCs), and the ERCs at the positive peak ERP electrode (dot, FIG. 2.1D) and the negative peak ERP electrode (dot, FIG. 2.1E) are shown in FIG. 2.1D respectively FIG. 2.1E. Twenty-four individual positive and negative brain activity data sets 6 (that is particularly the ERP traces at the indicated location) are plotted with thin grey lines and thick black lines depict the corresponding means. The areas in the dotted line boxes depict significant ERCs 7 and are greyscale-coded according to the usage attributes 3. The small arrow above the ERP traces 6 points at the stimulation S onset (i.e. 0 ms). FIG. 2.2F depicts scalp maps of the mean ERPs 6 and the corresponding goodness-of-fit estimate of the full regression model (R2) at three consecutive time points post-stimulation S. FIG. 2.2G-FIG. 2.2I depict scalp maps of the estimated ERCs 7 and the corresponding F-statistics for the three usage attributes 3. Note that both 'phone use per hour' and 'duration from peak' usage attributes 3 were significantly related to the ERPs 6 across several electrodes. See also FIG. 4. ERCs are also referred to as B values.

Figure 3:
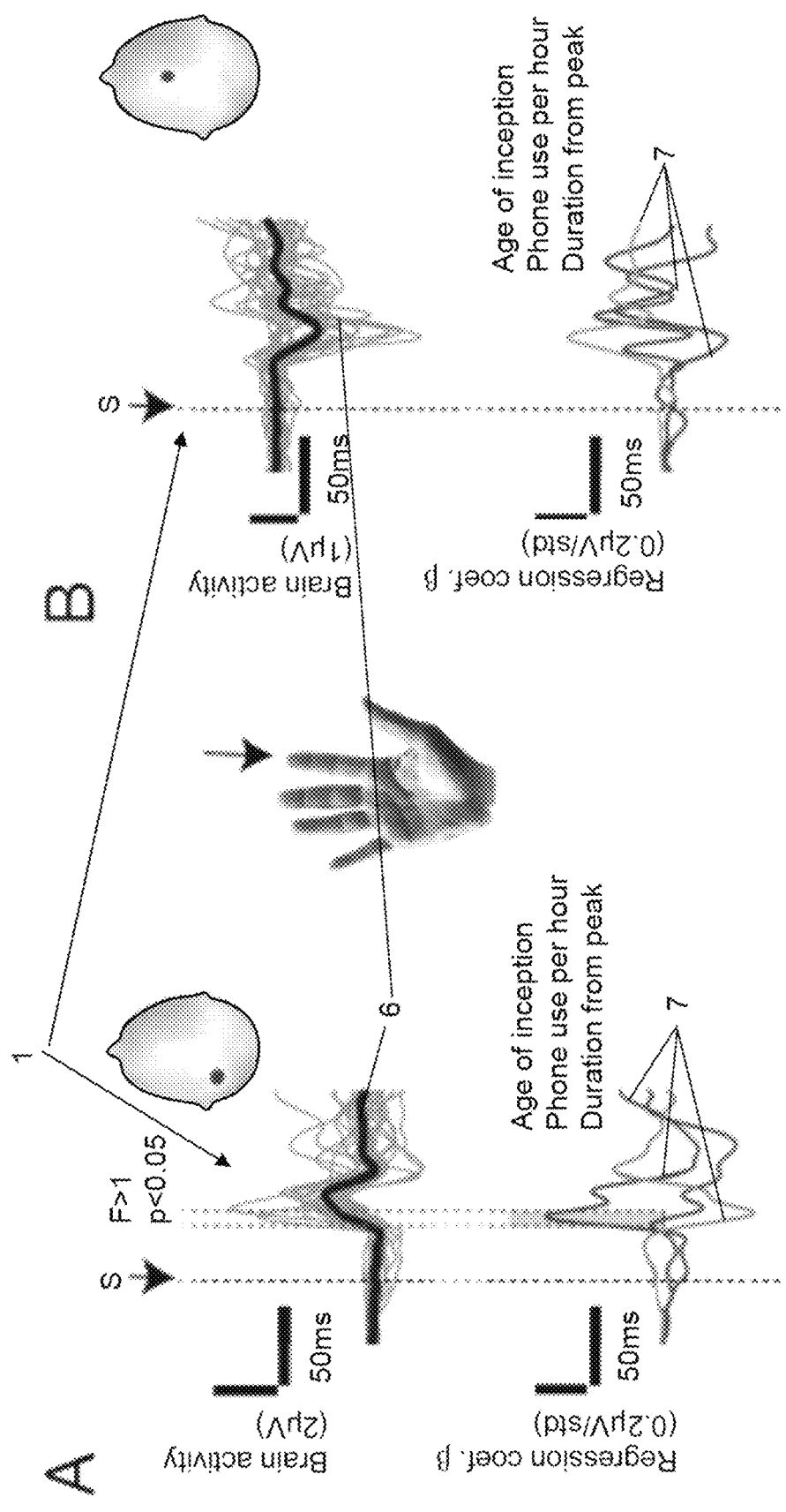
Figure 3:
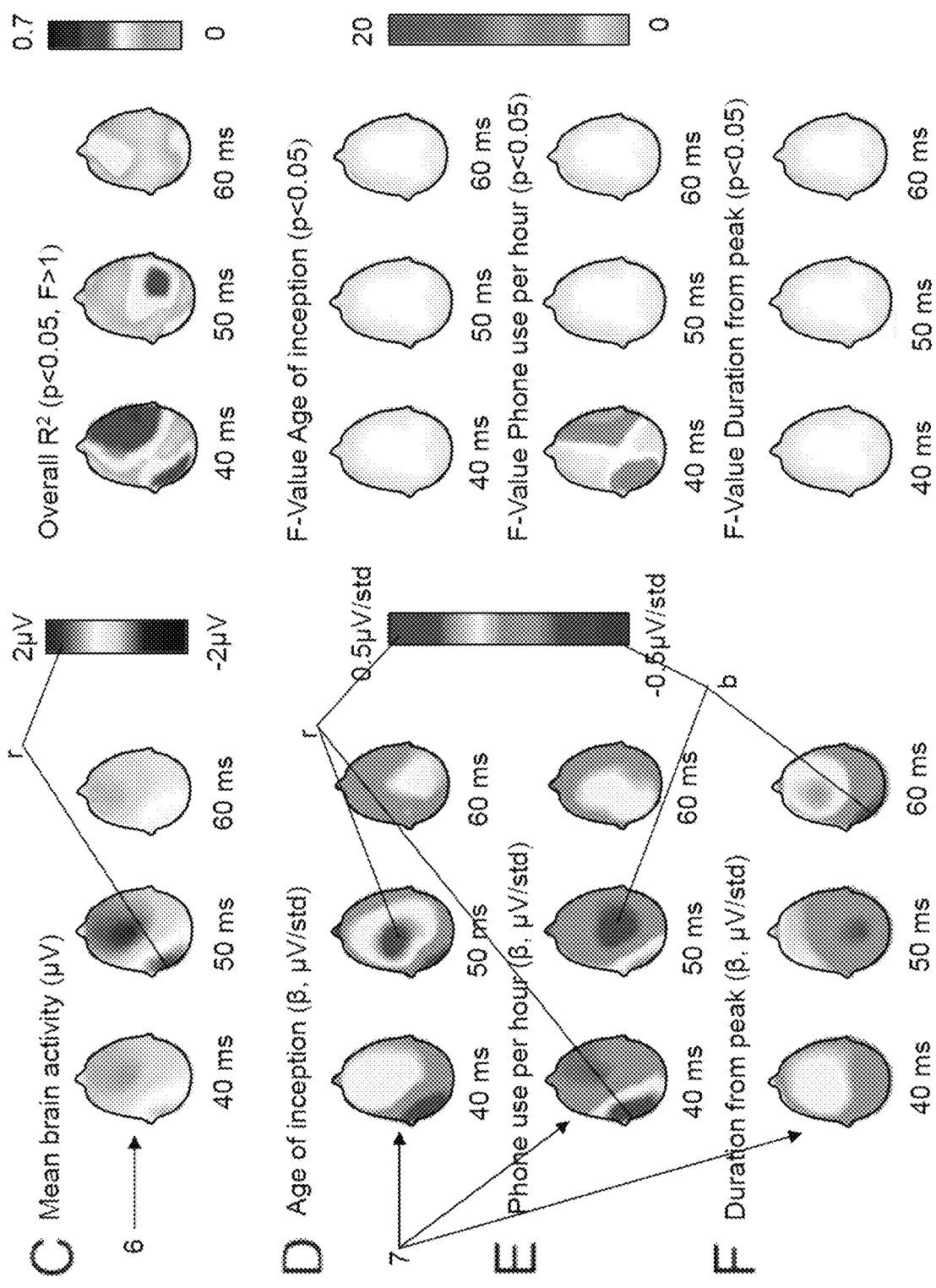

FIGS. 3.1 and 3.2 show the 'phone use per hour' usage attribute 3 in relation to the index finger ERPs 6. The same usage attributes 3 as illustrated in FIGS. 2.1 and 2.2 for the thumb ERPs 6 were used for regression analysis to model the index finger ERPs. FIG. 3.1A depicts the location of the positive peak ERP electrode, the area in the dotted line box depicts the significant ERCs 7 (corresponding to the usage attribute 3 'phone use per hour'). FIG. 3.2C shows a scalp map of the mean ERPs 6 and the corresponding goodness-of-fit estimate of the full regression model (R2). FIG. 3.2D-FIG. 3.2F show scalp maps of individual ERCs 7 and the corresponding F-statistics. The same conventions are used as in FIGS. 2.1 and 2.2. See also FIG. 4.

Figure 4:
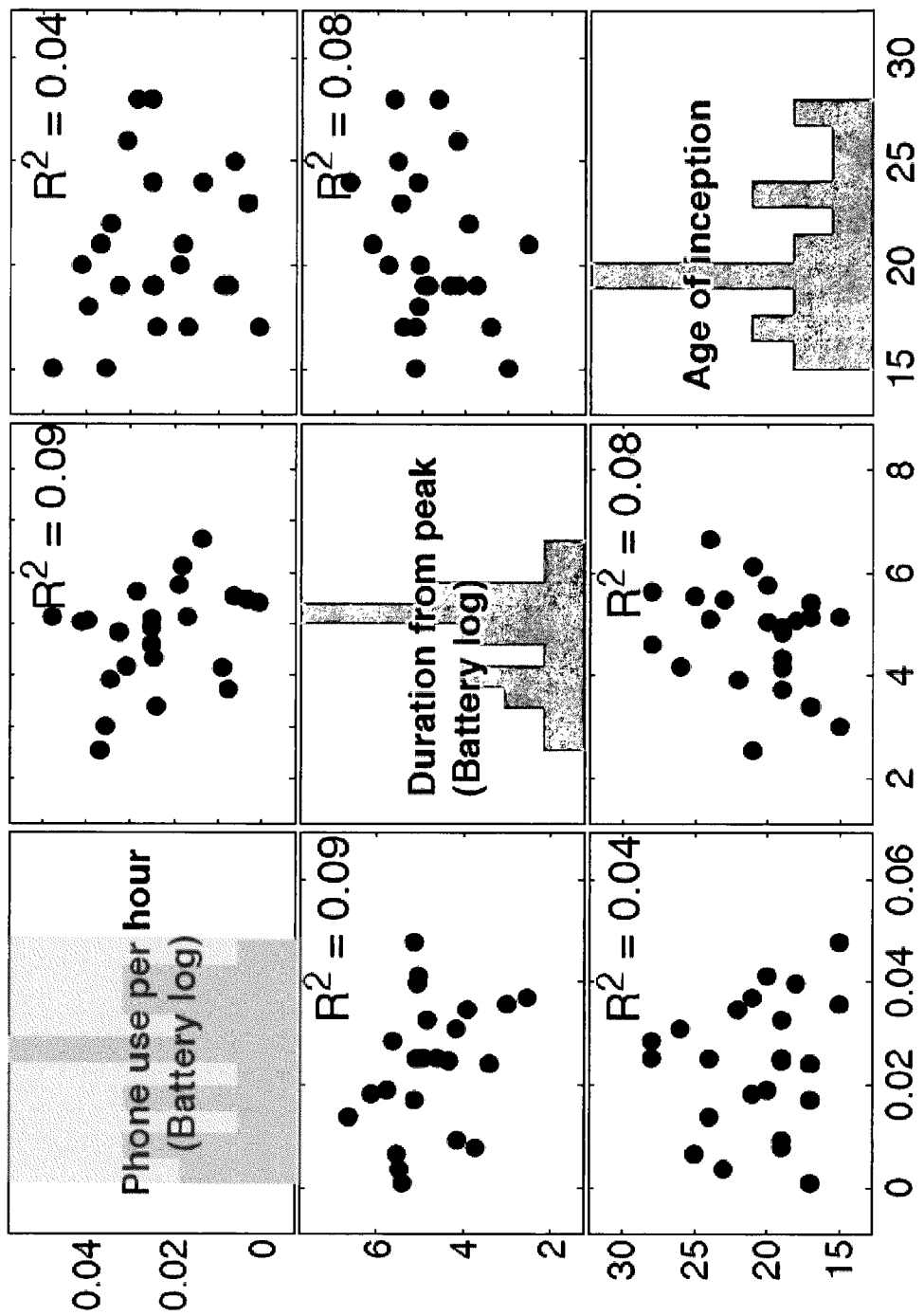
FIG. 4 shows scatter plots of the attribute data.

FIG. 4 shows a scatter plot matrix of the 3 independent usage attributes described in FIGS. 2.1A-C (with histograms) used towards regression analysis, and shown here prior to Z' normalization. Note the absence of correlations between the pairs of the usage attributes, and the corresponding R2 values mentioned for each plot.

FIG. 5 to FIG. 11 show flowcharts of different embodiments of the invention.

In the following embodiments at least one usage data set 2 is generated 100 by a person on a personal device 10, 1', N.

Figure 5:
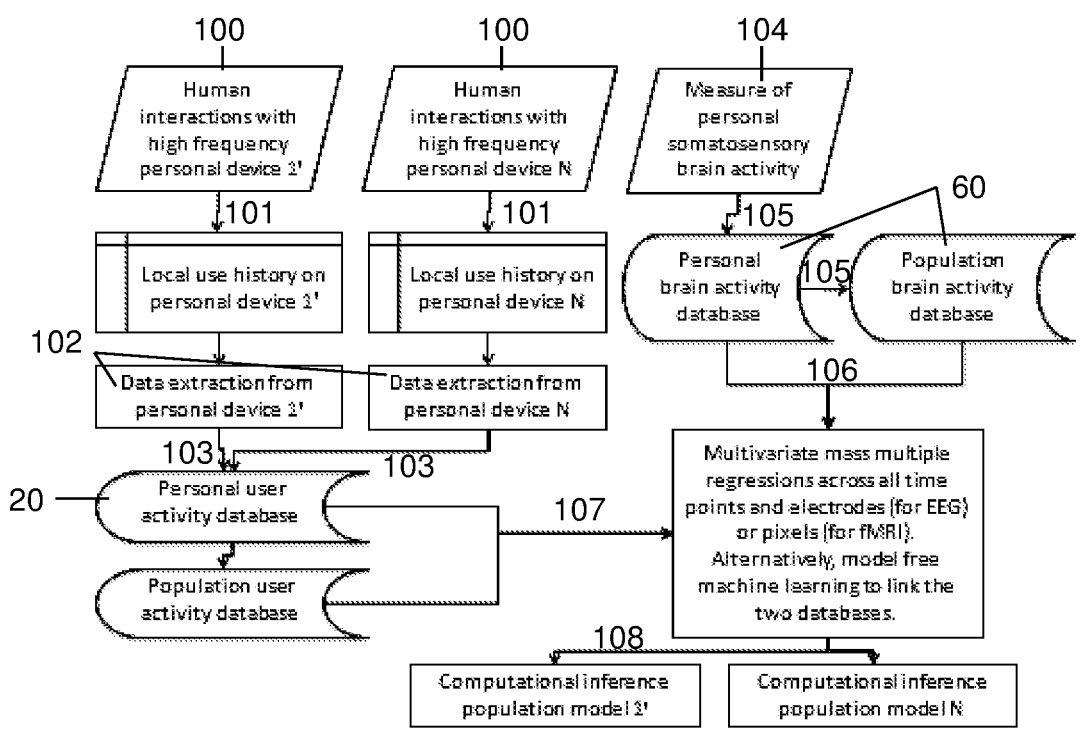
FIG. 5 shows a flowchart according to an embodiment of the invention.

FIG. 5 shows a flowchart outlining one embodiment of the method according to the invention, particularly how the computational inference model 5 is generated.

Usage data 2, also referred to as a usage data set 2, is generated 100, particularly from a plurality of persons on different personal devices 1', N. The usage data sets 2 are then stored 101 on the personal device 1', N. From there, attribute data 4 are extracted 102 from the stored usage data sets 2 and said attribute data 4 are stored in a usage data base that particularly can be a database where only attribute data 4 or usage data 2 of the same person are stored (personal database 20) or it might be that the attribute data 4 or the usage data sets 2 are stored in a common usage data base (population database) or in both kinds of usage databases.

Attribute data 4 is then submitted 107 to the regression analysis in order to generate 108 a computational inference model 5, for each person.

Furthermore brain activity data sets 6 are acquired 104 by one of the above outlined methods (e.g. EEG or fMRI). Said brain activity data sets are stored 105 in a personal or population database 60 or in both kinds of databases, analogous to the usage data base. Then the brain activity data sets 6 are submitted 106 to the regression analysis in order to generate 108 said computational inference model(s) 5.

Figure 6:
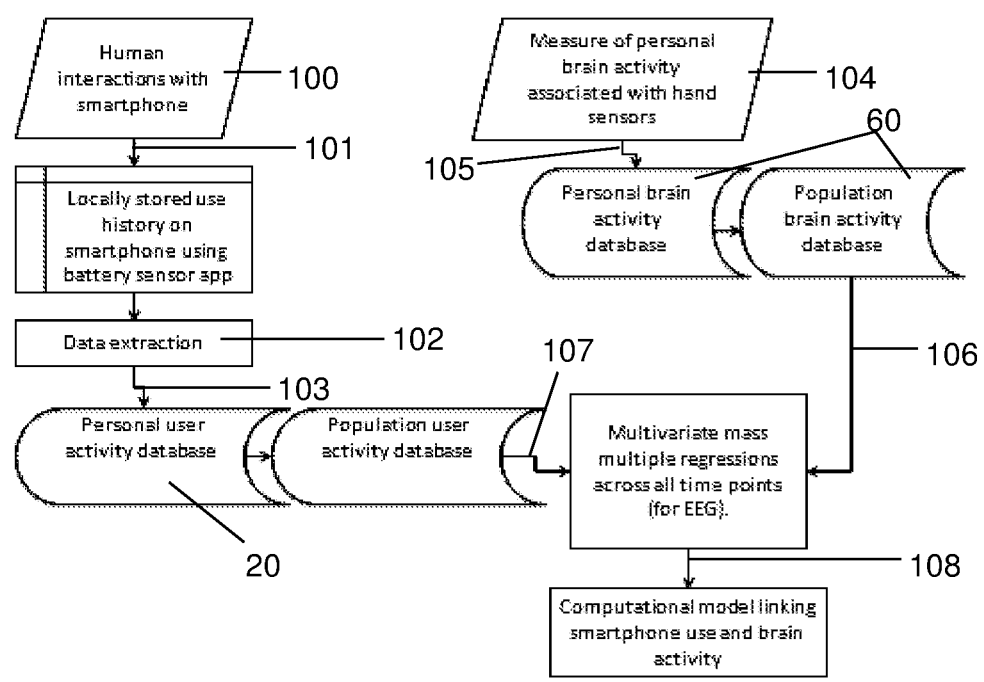
FIG. 6 shows a flowchart according to an embodiment of the invention.

FIG. 6 shows a flowchart of an embodiment according to the invention. Again usage data sets 2 are acquired 100 on a personal device 10, particularly a smartphone of one person. The usage data sets 2 are stored 101 on the personal device 10 until the attribute data 4 are extracted 102 from the local storage of the personal device 10, e.g. when the person connects the personal device with the internet or another network. The attribute data 4 is then stored 103 on a usage database that might be a personal database 20 and/or population database as explained above. From there, the attribute data 4 is submitted 107 to the regression analysis together with brain activity data sets 6 that have been previously acquired 104 and stored 105 on a brain activity data base 60 like e.g. a server. The regression analysis subsequently estimates 108 a computational inference model 5.

Figure 7:
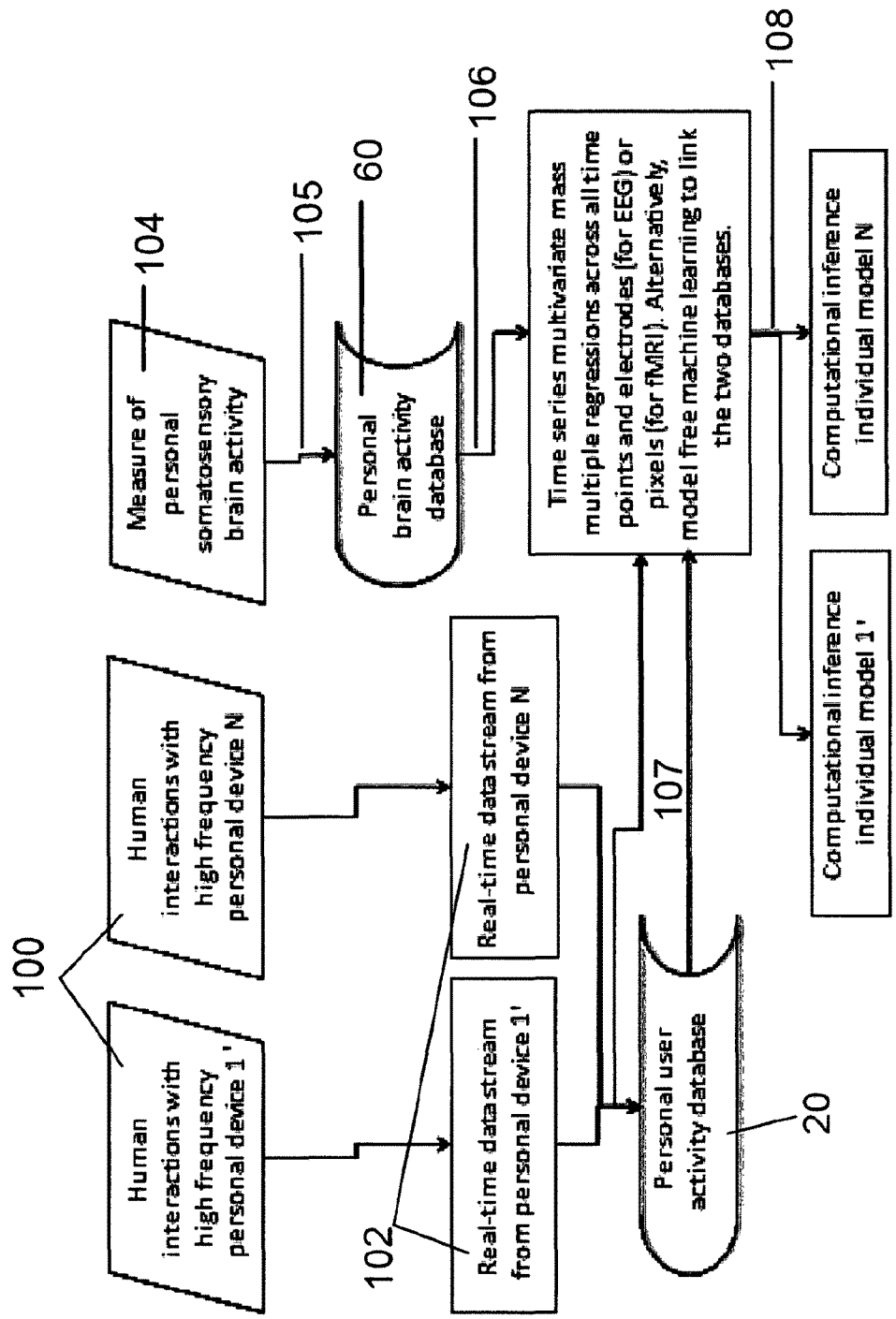
FIG. 7 shows a flowchart according to an embodiment of the invention.

FIG. 7 shows a flowchart according to one embodiment of the invention. Again usage data is acquired or recorded 100 by a personal device 1', N. Here the usage data 2 is processed from a plurality of persons, wherein the usage data 2 or the attribute data 4 is streamed, e.g. via an internet connection to the usage data base. from there the attribute data 4 is submitted to the regression analysis 107 as well as the brain activity data sets 6 of the plurality of persons. The regression analysis then generates a computational inference model 5 for each of the person of the plurality of person, particularly by using only attribute data 4 and/or brain activity data sets 6 form said person.

Figure 8:
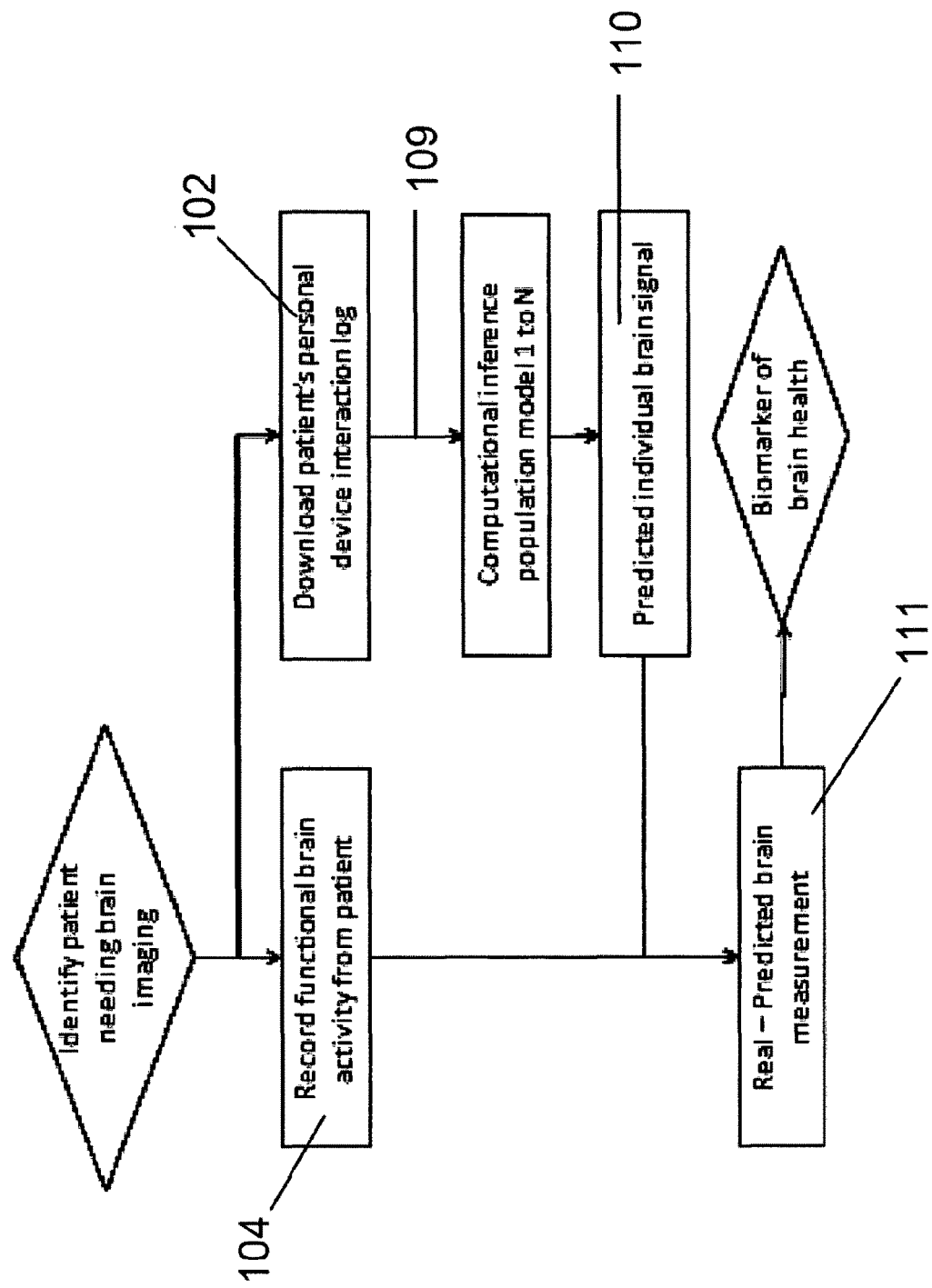
FIG. 8 shows a flowchart according to an embodiment of the invention.

FIG. 8 shows a flowchart of one embodiment of the invention. Here the predicted brain activity response 1 from the computational inference model 5 that is fed with attribute data 4 from the person of interest is compared 111 to a measured brain activity data set 6. From the deviations is might be possible to conclude on a biomarker of brain health.

Figure 9:
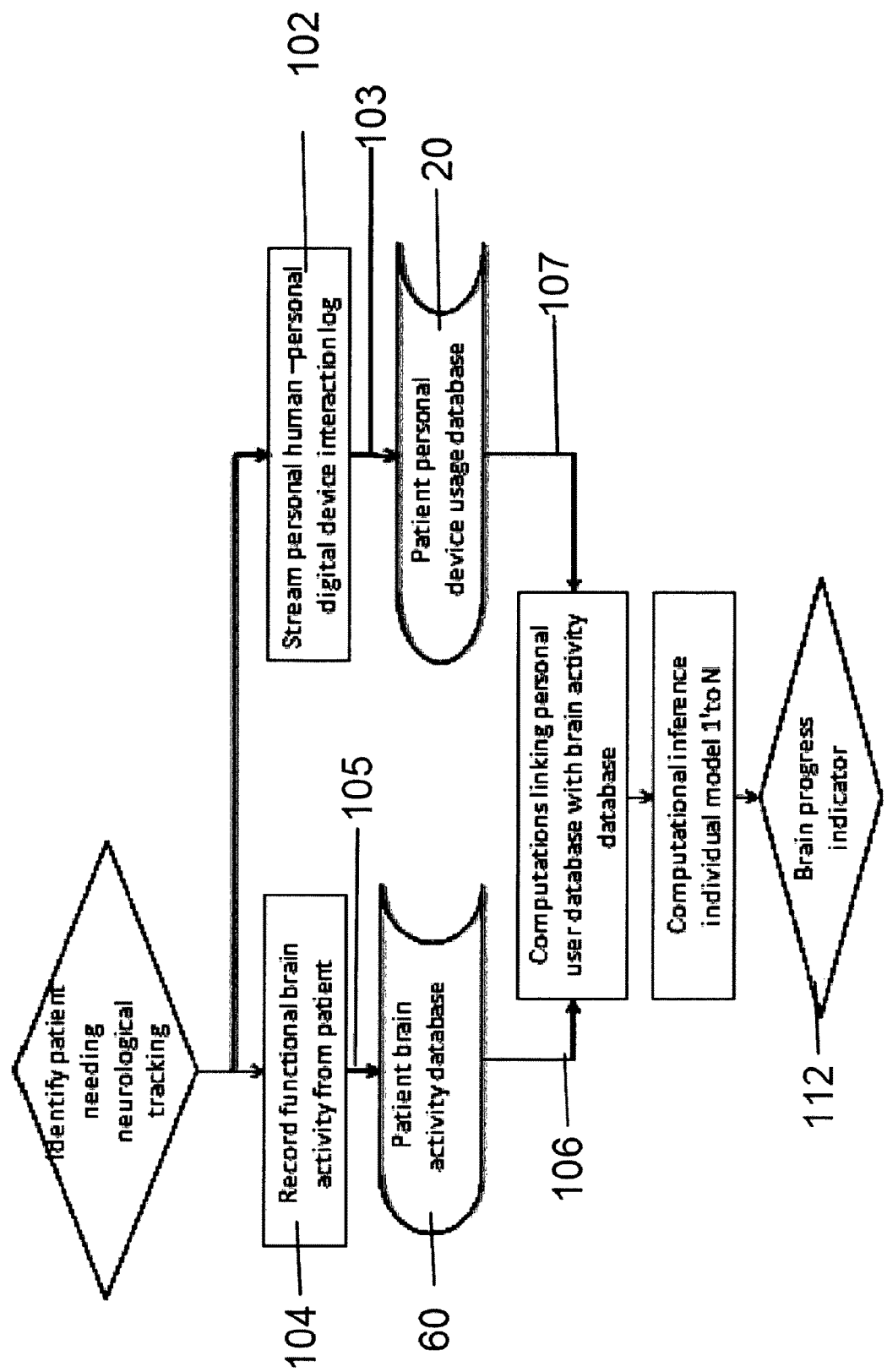
FIG. 9 shows a flowchart according to an embodiment of the invention.

FIG. 9 shows a flowchart of one embodiment of the invention. Brain activity of a person is measured 104 and stored 105 in a brain activity data base 60 and submitted 106 to the regression analysis. Also the acquired usage attribute data 4 are submitted 107 to the regression analysis. The computational inference model 5 can then be used to track brain activity response alterations in time, if the outlined method is performed repeatedly over time.

Figure 10:
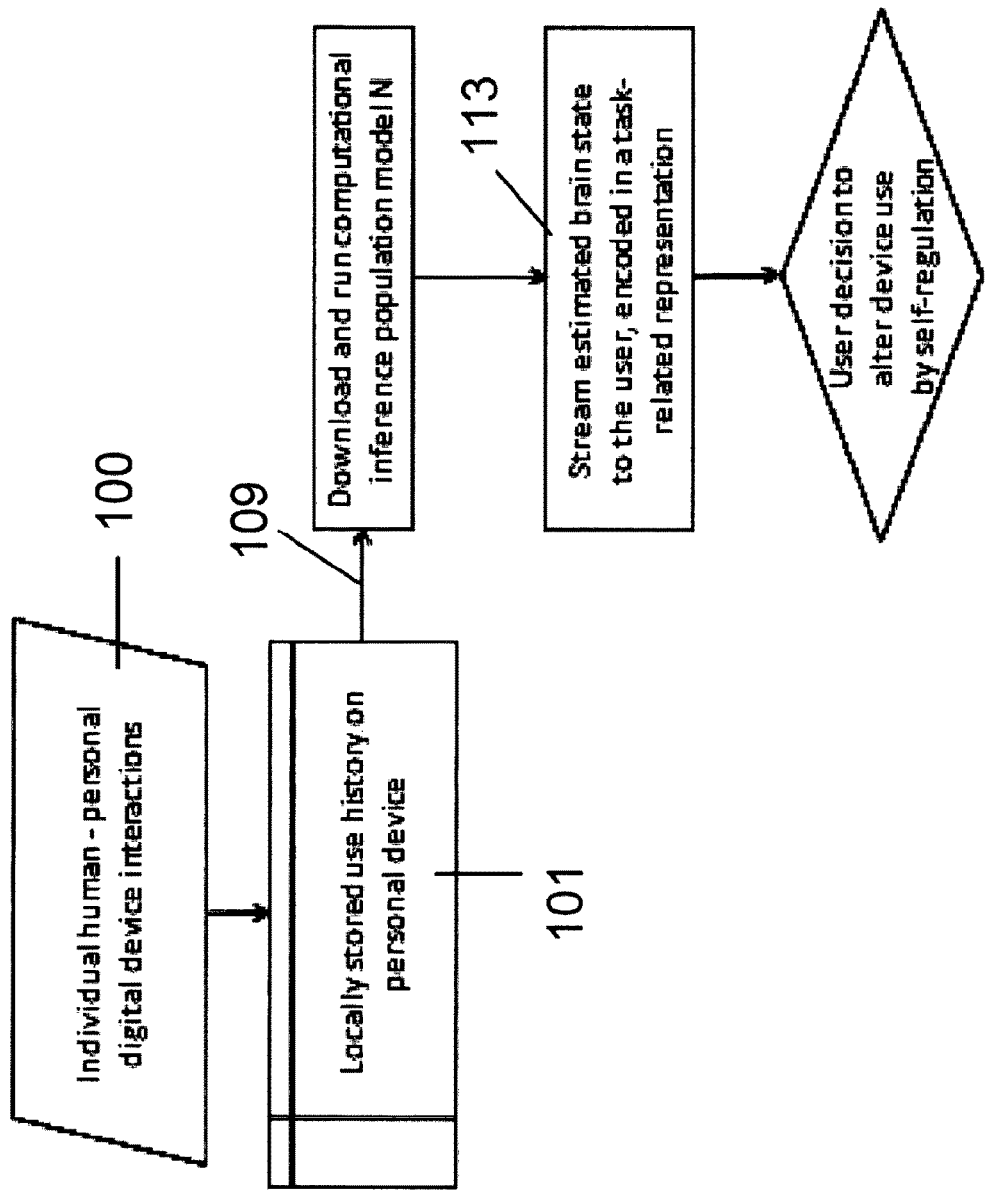
FIG. 10 shows a flowchart according to an embodiment of the invention.

FIG. 10 shows a flowchart of one of one embodiment of the invention. the acquired 100 and locally stored 101 usage data set 2 is submitted 109 to a computational inference model 5, that has been generated. The computational inference model 5 will then display 113 the predicted brain response 1 to the person, particularly on the personal device 10. The person is then enabled to particularly change usage behaviour due to a strong impact of the personal device use on its brain response 1.

Figure 11:
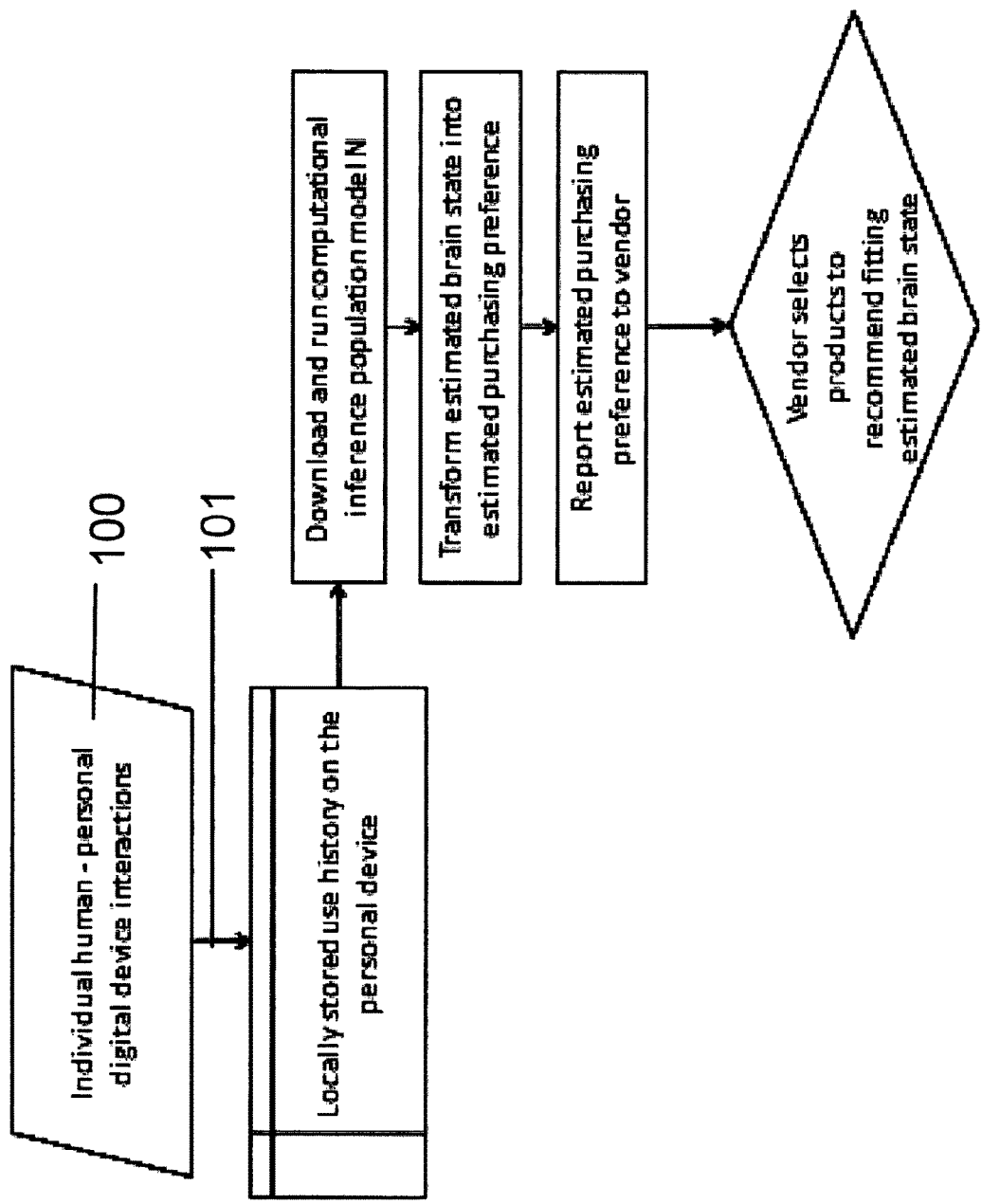
FIG. 11 shows a flowchart according to an embodiment of the invention.

FIG. 11 shows a flowchart of one of one embodiment of the invention. Here the attribute data 4 are submitted to the computational inference model 5. the computational inference model 5 will then predict a potential purchasing preference to a vendor if the estimated brain response 1 suggests.

FIGS. 12.1 to 12.5 show Inter-touch intervals (ITI) follow a power-law distribution. FIG. 12.1a: ITI distribution for one representative subject (black line BL) showing the power-law distribution (power-law exponent for this subject: $\alpha=1.734$). FIG. 12.2b: same as FIG. 12.1a, but for 84 subjects (gray lines GL). Black line BL denotes the ITI for the set of touches from all the subjects. Inset shows the distribution of a across the different subjects. FIG. 12.3c: Illustration of the priority model. (left) distribution of priorities for the touchscreen tasks (red) while the priorities for the other tasks are uniformly distributed (black). (Right): if the priority of a touchscreen task (red) is larger than the priority of another task (black) and if the permission is on, then an event (tap) is produced (solid vertical line) and a new task is taken from the touchscreen priority distribution. If the permission is off, then another task is executed instead of the touchscreen task (dashed vertical lines). FIG. 12.4d: Distribution of the inter-touch intervals for the priority model. Black line BL: analytics, red crosses RC: detailed model, blue circles BC: coarse grain model (see supplementary information). FIG. 12.5e: The priority index k (which is a model parameter that describes the relative priority of touchscreen tasks) is directly related to the power-law exponent $\alpha$ (which can be estimated from experiments). The analytics, $\alpha=2+k$ (black line BL) correspond well to the simulations (blue circle BC).

FIGS. 13.1 and 13.2 show simple reaction times in response to tactile inputs on the thumb tip are correlated to touchscreen behavior. FIG. 13.1a: The distribution of reaction times in a representative volunteer, and the distribution fitted with a three parameter ex-Gaussian function (black line BL). FIG. 13.2b: Added value plot of the full multiple regression model, illustrating the collective significance of the independent touchscreen variables—log number of touchscreen touches per day, $T_{min}$ and the power-law exponent $\alpha$—in predicting the reaction time skew (n=82). Confidence bounds around the fitted line are set at 95%. Note that a non-significant multiple regression would have permitted a horizontal line to fit the plotted data points. FIG. 13.2c: Effects of the touchscreen parameters on the reaction time skew and the skew was exclusively related to the a. FIG. 13.2d: Scatter plot showing the relationship between reaction time skew and a after adjusting for the remaining variables in the multiple regression.

FIGS. 14.1 to 14.4 shows sensory evoked potentials recorded from the scalp are correlated to the touchscreen behavior. FIG. 14.1a: The time-course of the evoked potentials recorded at an electrode over the somatosensory cortex illustrates the person-to-person variations in the signals evoked by the same stimulation at the thumb tip. Each individual is depicted with a grey line. The parts of the signal that were significantly related to the touchscreen parameters according to multiple regression (red). The corresponding event related coefficients and the significant relationships are in color. FIG. 14.1b: Topology of the signals and regression strengths at the two time points that capture the distinct temporal components of the significant relationships discovered here. FIGS. 14.2*c-e*: The topology of event related coefficients (β) for each of the three touchscreen parameters and the corresponding F statistics. FIG. 14.3*f*: same as FIG. 14.1*a*, but the stimuli was at the index finger tip. Similarly, FIG. 14.3*g* same as FIG. 14.1*b* and FIGS. 14.4*h-j* same as FIGS. 14.2*c-e*.

EXAMPLES

In the following a more detailed description of the invention is presented with references to specific aspects of the Figures.

Example 1 A first study was conducted on 38 healthy right-handed mobile phone users aged between 19 and 34 years old (median 22.9; 18 males and 20 females). Among them, 27 were smartphone users (median 22.9; 12 males and 15 females) and 11 were old-technology mobile phone users (median 23.2; 6 males and 5 females). The volunteers, all university students, were recruited via mass emails and lecture hall announcements. By using self-reports hand injuries, history of neurological disorders and medications that might have affected the nervous system were eliminated. The volunteers' handedness was confirmed by using a questionnaire. One person (female touchscreen phone user) chose to drop out of the study by missing the brain measurement and was eliminated from all analyses. In this study, any mobile phone with a fast processor and full front panel touchscreen such as iPhone and Samsung Galaxy is considered a smartphone as opposed to an old-technology mobile phone lacking such features.

Mobile phone use survey and battery logs:

All volunteers were probed on mobile phone use behaviour by using a questionnaire. This was used to extract the number of years since the volunteers owned a smartphone (i.e. leading to the usage attribute and the corresponding attribute data 'age of inception') and/or an old technology phone, to document the mobile phone model, to list any other personal digital technology owned, to estimate the time spent on the phone and to specify the mode of interaction (stylus, voice or touch). The questionnaire also included a list of 18 hand/finger postures on a smartphone and touchscreen phone users were instructed to rank them from the most favoured to the least favoured posture. Similarly, mobile phone activities were also ranked from a list of 11 actions that included text messaging and phone calls. Furthermore, the typing actions and grip style of all volunteers were also documented by using a 480 fps camera.

To quantify use in a non-intrusive manner prior to the brain activity measurements the battery logs from touchscreen phones were evaluated over a period of 10 days. However, such quantifications could not be performed with the old-technology (non-touchscreen) phones due to the lack of easy access to the battery sensors. All the touchscreen phones included in this study used similar batteries, with manufacturer's specifications on the battery life ranging between 6-8 hours of talk time on 3G, 10-14 hours of talk time on 2G, 4-7 hours of web use over 3G and 7-10 hours of web use over Wi-Fi. The percentage of battery power was registered every 10 min when the phone was in use by using the DataWiz app (Princeton EDGE Lab, USA). The change in state of the battery over time was quantified by using differences between consecutive samples (MATLAB® R2011b, USA). The negative differential indicated battery drain and the positive differential indicated gain such as in charging of the phone. Because only in phone use is of interest, all positive values were set to 0, and remaining absolute values were used for further analysis. The usage data were smoothed using a 50-min moving window. The area under the differentials divided by the entire recording period (in h) as well as the natural log of the time interval from the differential peak (from the entire recording period) to the time of brain measurement were extracted using MATLAB®. The app malfunctioned in 2 volunteers due to user errors and the corresponding usage data were eliminated for further analysis.

Tactile stimulations and electroencephalography (EEG):

The thumb, index and middle fingertips of the right hand were randomly stimulated by using solenoid tappers (Heijo Research Electronics, UK) which could be precisely computer-controlled in time via a stimulation box by using a home-made script running on MATLAB®. The tappers applied a 2 ms-long circular supra-threshold touch stimulus with an interstimulus interval of 750 ms±250 ms and made a 12.5 mm$^2$ contact with the fingertips. Stimulations were randomly delivered either individually to the 3 fingertips or simultaneously to the thumb and index fingertips. In order to cover the noise made by the tappers a background white noise was made audible via headphones. The EEG data were acquired from 62 electrodes mounted on an elastic cap (EasyCap, Germany) and distributed equidistantly to cover the entire scalp. Two additional electrodes were used for electro-oculogram (EOG) to monitor eye movements. The electrode locations were digitized in a 3D nasion-ear coordinate frame (ANT B.V., The Netherlands and Xensor software) for a representative volunteer. The EEG signals were recorded against the vertex and amplified with an AC coupled amplifier (BrainAmp, Brain Products GmbH, Germany). The data were sampled at 1000 Hz, digitized using a 16-bit AD converter, and re-referenced offline to the average signal from all the scalp electrodes (EEGLAB, an open source MATLAB® toolbox, USA). The data were further analyzed with EEGLAB to band-pass filter between 1 and 80 Hz. All epochs that exceeded a ±70 μV threshold were eliminated to reject eye blinks from the analysis. Furthermore, trials containing statistically 'abnormal' amplitudes were defined and eliminated using the kurtosis and joint probabilities of the recordings (the threshold was set at 5 std), and finally, eye movement artifacts and facial movement artifacts were rejected by using independent component analysis (EEGLAB). Event-related potentials (ERPs) for each stimulus location were obtained by averaging 1250 corresponding stimulations. Brain activity at each time point (−50 ms to 120 ms; 0 ms=stimulus onset; −50-0 ms=baseline) from each electrode and for each stimulus location was analysed with a linear modelling approach. The two-sample t-tests and multiple linear regressions (and the corresponding F-tests) were corrected for multiple comparisons using 2D spatiotemporal clustering based on 1000 bootstraps. All the statistical and clustering analyses were conducted with LIMO EEG (MATLAB® toolbox, using EEGLAB) and these tests are described in detail in "Pernet, C. R., Chauveau, N., Gaspar, C., and Rousselet, G. A. (2011). LIMO EEG: A Toolbox for Hierarchical Linear MOdeling of ElectroEncephaloGraphic Data. Computational Intelligence and Neuroscience 2011, 11".

37 right-handed persons were chosen, 26 of them used touchscreen phones and 11 of them used old-technology mobile phones. Questionnaires provided few key insights into how the more modern phones were used. Firstly, touchscreen users primarily used their right thumb on the screen as opposed to other fingers (8%), and none of them used a stylus. The thumb preference was expected given that hand-held phones were designed as such. Secondly, in agreement with a US national survey on smartphone use, 80% of the touchscreen users in this example mainly used their phone towards receiving and sending text messages or email, as opposed to passively listening to music, watching videos or making calls. Finally, according to the self-reports, touchscreen users spent noticeably more time with their phone than the nonusers.

It was investigated whether the somatosensory cortical electrical activity evoked from the fingertips differed between touchscreen phone users and nonusers. Sixty-two surface electrodes distributed over the entire scalp were used to detect cortical potentials evoked by touch on the thumb, index and middle fingertips of the right hand. Each tactile stimulus consisted of a light mechanical contact that lasted for 2 ms, and event-related potentials (ERPs) were based on 1250 stimulations on each fingertip. For all three fingertips tested both in touchscreen users and nonusers, the touch resulted in a dipole field around the contralateral (to stimulation) somatosensory cortex with signal onset at 32 ms and peak at 55 ms (on grand mean traces). The positive ERPs were detected in the contralateral parietal electrodes and the negative signals were detected more medially in the contra- and ipsilateral frontal electrodes (FIG. 1.1C-FIG. 1.2H).

Based on the latency and signal topology, it could be asserted that these signals originated from the primary somatosensory cortex. We analysed the signal differences between the smartphone users and nonusers across all time points (50 ms pre-stimulation to 120 ms post-stimulation) and for each electrode by using two-sample t-tests corrected for multiple comparisons using 2D spatiotemporal clustering. For all the tested fingertips the amplitude of the positive ERP was larger in touchscreen users compared to nonusers (FIG. 1.1C-FIG. 1.2H). Temporally, the positive signals differed between 39-68 ms for the thumb, between 38-60 ms for the index fingertips, and between 48-66 ms for the middle fingertip (FIG. 1.1C, E, G). Spatially, the statistical maps revealed that the differences were clustered on the contralateral parietal scalp for all the three fingertips (FIG. 1.1D, F, H). However, the spatial extent of these differences was the smallest for the middle finger (FIG. 1.2H).

In short, touchscreen users relied mostly on their thumb to interact with the screen but the cortical potentials associated with the first three fingertips were enhanced in comparison to the nonusers.

The increased cortical activity in touchscreen users compared to nonusers could be due to a more intense usage of the hand, in the sense that the former group used the right thumb more than the latter group did. Alternatively, it could be due to the development of touchscreen-specific motor routines or 'skills' as the movements associated with push buttons (in nonusers, using only old-technology mobile phones) vs. taps or swipes on a screen (in smartphone users) were distinct. To investigate whether the cortical alterations scaled corresponding to touchscreen use, three different usage attributes related to phone use were identified: first, the self-reported age at which volunteers started using their smartphone ('age of inception). This usage attribute was inspired by previous reports on elite musicians and athletes where the somatosensory representation of the corresponding body part was linked to the age at which practice began. Second, the history of phone use over a 10-day period was quantified by using built-in battery logs. Essentially, as the battery was drained with each phone use, the logs provided a proxy measure of finger-touchscreen interactions with a 10-min resolution and the data were smoothed using a 50-min moving window. The area under this curve was divided by the length of the recording period to derive the usage attribute 'phone use per hour' (FIG. 2.1B). Third, using the same smoothed battery signals we estimated the time elapsed from a period of intense use—defined as the peak of battery drain—to the time of EEG measurement and referred to as the usage attribute 'duration from peak', FIG. 2.1C, see also FIG. 4 for scatter plot matrix using the three attributes and their associated attribute data). Based on preliminary simple linear regression between this measure and brain activity, we used the natural log of hours elapsed from the peak. Multiple regression analysis was conducted using the attribute data associated to the respective usage attribute (Z' normalized) for all time points (50 ms pre-stimulation to 120 ms post-stimulation) and across all electrodes, resulting in a corresponding event-related coefficient (ERC) for each usage attribute. The regression statistics were corrected for multiple comparisons using 2D spatiotemporal clustering.

For the thumb tip, at the electrode with maximum mean positive ERP (grand mean of touchscreen user group) the corresponding ERC for the usage attribute 'phone use per hour' was also positive and this linear relationship was significant between 33-44 ms and 53-61 ms (FIG. 2.1D). Essentially, the higher the amount of phone use in the preceding 10 days, the larger was the signal at the rising edge, peak and falling edge of the positive ERP. At the electrode with the maximum mean negative ERP amplitude the ERC corresponding to the usage attribute 'duration from peak' was significantly positive between 56-68 ms (FIG. 2.1E). In other words, the longer the time elapsed from a period of intense use, the lesser the signal at the falling edge of the negative ERP.

Scalp maps of the ERCs and the corresponding statistics captured the widespread impact of phone use (FIGS. 2.2F-I). Overall, according to the R2 value of the linear computational inference model, up to 60% of the inter-individual variation in cortical activity could be explained by the chosen variables (FIG. 2.2F). Focusing on individual ERC scalp maps, for the usage attribute 'phone use per hour' the electrodes that detected positive ERP showed positive ERC and the negative ERP electrodes showed negative ERC (FIG. 2.2H). The pattern was distinct for the usage attribute 'duration from peak'—here only the negative ERP electrodes were related to the attribute data of the usage attribute 'duration from peak' and the relationship was reversed, i.e. the negative ERP electrodes showed positive ERC (FIG. 2.2I). Although the spatiotemporal pattern of the ERC corresponding to the usage attribute 'age of inception' appeared converse to the ERC corresponding to the usage attribute 'phone use per hour', no significant relationship was found between this usage attribute and brain activity (FIG. 2.2G).

For the index fingertip, the linear relationships at the maximum positive and negative ERP electrodes were more restricted than for the thumb tip (FIG. 3A-B). Essentially, a significant relationship was found between the 'phone use per hour' usage attribute, respective attribute data, and ERP, but only for the positive electrode between 32-43 ms. Simply put, the more the phone was used over the preceding 10 days, the larger was the signal on the rising edge of the positive ERP. According to the scalp maps, the positive ERP electrodes showed positive ERC (FIG. 3E). The rest of the usage attributes, respective attribute data, did not show any significant relationship to brain activity (FIG. 3D, F). Nevertheless, up to 54% of the variations were explained by the linear model (FIG. 3C). For the middle fingertip, no significant ERC were found, although the linear model explained up to 55% of the variation. In sum, the cortical potentials associated with the thumb and index fingertips reflected the touchscreen phone use history recorded by using the 10-day battery logs. The cortical activity evoked by touch to the thumb tip was directly proportional to the amount of phone use over the past 10 days and inversely proportional to the time elapsed from a period of intense use. The potential evoked by touch to the index fingertip was also related to the amount of use, albeit to a lesser extent, and not related to the latter usage attribute.

Inter-fingertip inhibitory interactions are not eroded by the touchscreen phone use:

When neighbouring fingertips are simultaneously stimulated the magnitude of the ERP is smaller than the arithmetic sum of signals from the corresponding individual stimulations. This difference is theoretically explained by cortical lateral inhibitory interactions between the neighbouring fingers. The increased cortical activity associated with individual fingertips in touchscreen users may have come at the cost of such inhibitory interactions. Essentially, unmasking the inhibition between the neighbouring fingertips may have contributed to the larger potentials in the touchscreen users. To address this issue, the difference between the predicted and real ERPs in response to simultaneous stimulation of the thumb and index fingertips were measured. The touchscreen users were compared to the nonusers by using two sample t-tests across all electrodes and time points (50 ms pre-stimulation to 120 ms post-stimulation), and corrected for multiple comparisons using 2D spatiotemporal clustering. Interestingly, the proxy measure of inhibition was significantly enhanced in smartphone users compared to the non-users between 40-57 ms.

Therefore, the increased cortical signals in touchscreen phone users were not associated with a loss of intra-cortical inhibitory activity.

At first glance the increased cortical activity in touchscreen phone users compared to nonusers appears similar to what occurs in musical string players. But a more detailed examination reveals two notable differences: the age at which musical practice began was strongly and linearly related to the cortical activity evoked from the little finger. However, this link between the age of inception and the cortical activity was not significant for touchscreen users. Furthermore, a daily dairy of musical practice was maintained for a week, analogous to the 10-day battery logs used here: while the musicians did not show any linear relationship to the recent activity, the touchscreen users did.

Based on the 10-day battery log versus brain activity correlations alone, it was not clear if cortical processing was shaped by phone use over the past 10 days. Essentially, did the 10-day log reflect use over the past 10 days only or was this log representative of use over a much longer period? For instance, the phone use levels may have remained stable over months and gradually shaped the cortical processing but due to the stable usage the cortical signals may have still correlated well with the recent log.

Although the rapidly transient cortical alterations were limited to the thumb, the cortical potentials from all the first three fingertips were enhanced in touchscreen users compared to nonusers. Moreover, we unlocked a new method to nonintrusively quantify daily hand use by using battery logs and this could be used to calibrate somatosensory potentials in basic and clinical neurophysiology.

Example 2

The details of how people behave on mobile devices have profound personal, social, economic and political implications, but the neuronal basis of this behavior is not known. Previous observations in individuals with elite skills, such as in concert musicians or blind Braille readers, raise the possibility that the fine-grained behavior expressed in the real world can be traced to the cortical processes that are directly engaged with the periphery[1-5]. Here, as a second example, we show that in a young adult population the behavioral details captured by recording the timings of each touchscreen event on the smartphone is correlated to sensorimotor cortical activity. We found that the inter-event times followed a power-law distribution ranging from fraction of a second to several hours. The power-law exponent ranged between 1.5 and 2.1, and this variance could be theoretically explained by how individuals prioritized their touchscreen interactions over all other actions. The number of events also varied from person to person. The higher the power-law exponent the more predominant were the fast reactions in response to tactile inputs at the thumb tip, but the number of events were unrelated to the reaction times. The cortical signals measured by using electroencephalography (EEG) in response to tactile stimuli at the thumb and index fingertips were related to both the exponent and the number of touchscreen interactions. Interestingly these correlations were separated in time, such that the exponent was directly proportional to the amplitude of the long-latency cortical signals and surprisingly, the number of events was inversely proportional to the short- and long-latency signals. The inter-individual differences in how people stay informed and connected by using mobile devices may be partly explained by the configuration of the sensorimotor cortex.

Touchscreen smartphones are central to modern societies and ubiquitously used to communicate and seek information from the Internet. How access to this technology is related to the properties of the human brain is not clear. The popularity of smartphones suggests that touchscreen skills are commonly present in the population. However, the sensorimotor cortical activity of people who use touchscreen smartphones is distinct compared to those who use old-fashioned phones[6]. Presumably, the ways in which smartphones are used in the real world vary substantially from person to person. As the details of smartphone use can be seamlessly quantified by using the technology built-into the phones, the inter-individual variations in touchscreen behavior can be systematically related to the configuration of the human cerebral cortex.

We focused on right-handed university students well versed with smartphone technology; median age 24 years ($25^{th}$-$75^{th}$ percentile range is reported here and for the age it was 23-28 years, 41 females and 45 males) and median years of experience was 4 years (3-5 years). The narrow age and experience distributions helped us focus on the behavioral parameters captured on the touchscreen rather than the anticipated generational and developmental differences of this behavior. We recorded the timestamps of touchscreen events when the phone was in an unlocked state by using an app. The median period of recording preceding the neuronal measures was 34 days (20-44 days). Although people were free to use any finger on the screen, according to our survey the top three finger postures involved the right thumb alone (median rank 9 out of 10, 8-10), the right index finger alone (median rank 8 out of 10, 5-9) and the simultaneous use of both the thumbs (median rank 7 out of 10, 3.5-8). The next posture in terms of median rank was the left index finger alone (3 out of 10, 1-4). For simplicity and to limit the invasiveness of our observations we considered all touches as equal. Over the recording period individuals generated a median of 2829 touches per day (1725-4115 touches per day). According to maximum likelihood fitting method and Kolmogorov-Smirnov statistic the inter-touch intervals followed a power-law distribution (median KS D value 0.026, 0.021-0.037). The distribution was valid for intervals slower than $\tau_{min}$ with a median of 618 ms (484.5-832 ms). The power law exponent, 'α', varied from person to person and the population median was 1.82 (n=84, 1.74-1.89, FIG. 12.2). These values were non-overlapping with the exponents discovered for emails and library-loans, where the exponents were distributed around the value of 1, but they did overlap with the values found for outgoing phone calls in people who engaged in phone-sales or fraud, where the exponents were distributed around 2 and no volunteer was found to have a exponent smaller than 1.5[7-10]. Furthermore, the logarithmically normalized number of touches was related to α, such that the larger the α the higher the number of touchscreen touches per day (n=84, $R^2$=0.38, t=5.65, p=4.7×10$^{-10}$). Essentially, individuals who generated a higher number of touchscreen touches had smaller gaps between the touches across the broad timescale captured by the power-law.

Inter-individual variations apart, we examined the temporal stability of all the three measures—log normalized number of touchscreen touches per day, α and $\tau_{min}$. To elaborate, we reanalyzed the data from two consecutive 15-day blocks (the duration was arbitrarily chosen and ensured sufficient data points towards the power-law estimates) in a subset of volunteers who were recorded for at least 30 days and the measure from the first block was strongly related to the second block (n=55, $R^2$ values for α: 0.76, $\tau_{min}$: 0.89 and log touches per day: 0.84). The relationships were weaker when we reinstated the measurements with a gap of 2-3 months in a subset of the volunteers (n=30, $R^2$ values for α: 0.16, $\tau_{min}$: 0.60 and log touches per day: 0.47). In spite of the perceived complexity of human actions, social interactions and the environment, over a limited period individual actions at the level of touchscreen interactions can be simply predicted based on the data aggregated from the recent past.

Typically, smartphones remain well within the reach of the users at any given time and we simply modeled touchscreen behavior by using a single agent that continuously decided between touching the screen or doing something else. The decision to touch the screen was made if the touchscreen task had a higher priority than any other action. Intuitively, some people more frequently perceive touchscreen tasks to be of a higher priority than others. To capture this inter-individual difference the touchscreen priority values $x \in [0,1]$ were drawn from a distribution $P_k^T(x)=(k+1)x^k$ where k>−1 is the priority index. The priority values $y \in [0,1]$ for the other tasks are drawn from a uniform distribution. Therefore a priority index k>0 indicates that the touchscreen tasks have on average a higher priority than all other tasks (FIG. 12.3). In our model, as in real life, a higher priority was not enough to execute the decision to touch the screen and it could be reversed when the conditions were not permissive due to exogenous restrictions such as limited connectivity, lecture hall rules, drained battery or social norms of formal conversations. Again, intuitively, there are inter-individual differences in how people are exposed to and perceive such exogenous constraints and in our model we captured the variance by using a permission threshold that could acquire any value between 0 and 1, and was compared against values randomly drawn from a uniform distribution. From this simple priority-based model, we can numerically simulate as well as analytically compute the inter-event distribution and find that for $\tau > \tau_{min}$ (see supplementary information):

$$P(\tau) \sim \tau^{-\alpha}$$

where the power-law exponent α (which can measured empirically) is directly linked to the priority index k via the following relation α=k+2 and is independent of the permission threshold. Therefore by measuring the power-law exponent of one individual, we can deduce her priority to specific tasks (here touchscreen tasks) against all other actions. Interestingly, by ranking the median exponents from different tasks we get, library loans=sending email=making mobile phone calls (1)<checking online news (1.2)<printing (1.3)<using the smartphone (1.8)<and in some, making fraudulent calls or phone sales (2). Similar priority-based models have been used to explain the timing of email, mail correspondences and events generated by two interacting agents[8,9,11].

Next we focused our observations to discover how the data logged in the real world were related to the basic cortical sensorimotor processing evaluated in the lab. We addressed whether the speed of sensorimotor processing was related to touchscreen behavior by measuring simple reaction times in response to tactile input at the thumb tip. Based on previous reports on deliberate practice and the congenitally blind, we expected the higher the number of touches on the touchscreen per day the faster were the reaction times in response to the tactile input[12,13]. According to one well-explored and somewhat contentious theory in human motor learning the distribution of practice—in terms of massed or distributed practice—is an important determinant for motor performance[14-17]. However, as a heavy-tailed inter-event distribution is absent in deliberate practice, how power-law action distributions determines motor performance remains theoretically and empirically unexplored. Intuitively, reaction times were faster in individuals who generated touchscreen touches with fewer longer gaps or with a larger α. However, according to multiple linear regression analysis median reaction times were unrelated to the touchscreen behavioral parameters, α, $\tau_{min}$ and log touches per day (Multiple regression, n=82, $R^2$=0.06, p=0.179). Another possibility was that the sensorimotor processors increased the share of faster responses without shifting the median but by making the reaction time distribution more right skewed; such as in previous reports where the skew was increased with a stronger stimulus[18,19]. Interestingly, we found that the skew was directly proportional to α but not related to the other touchscreen parameters (Multiple regression, n=82, $R^2$=0.16, p=0.003; for parameter α, t=−3.15, p=0.002, FIG. 13.2). Although our experiment cut-off reactions slower than 1 s, the increased skew may have still originated from a few long reaction times due to lapses in attention such as in attention deficiency hyperactivity disorder[20]. We eliminated this possibility by using three parameter ex-Gaussian fits and found that the slow reaction times captured by the exponential part of the distribution did not show a significant relationship with the touchscreen parameters (Multiple regression, n=82, R2=0.02, p=0.754). In an ex-Gaussian, the spread of the Gaussian part is inversely proportional to the skew and we did find that this spread was inversely proportional to α (Multiple regression, n=82, $R^2$=0.126, p=0.014; for parameter α, t=−2.2, p=0.03).

So do the reaction time results mean that individuals with fewer longer gaps in touchscreen use produce the fastest actions on the touchscreen? We examined the relationship between the shortest inter-touch intervals (5 percentile, log normalized) and touchscreen parameters. We found that the touchscreen parameters were significantly related to the shortest intervals (Multiple regression, n=83, $R^2$=0.4, p=1.01×$10^{-9}$). Interestingly, the individuals who produced a higher number of touches also produced the fastest touches in terms of inter-touch intervals (parameter log number of touches per day: t-stat=−7.4, p=1.36×$10^{-10}$). Perhaps somewhat surprisingly, and contrary to what we expected from the reaction time results, the larger the a slower were individuals in terms of the shortest inter-touch intervals (t-stat=3.2, p=1.36×$10^{-10}$). The parameter $\tau_{min}$ was unrelated to the shortest intervals. Although tactile reactions in the lab are hastened in individuals with a larger α, in the real world the motor speed is slower in individuals with a larger α. These results also suggest that a and the number of touches have distinct neuronal correlates.

Next, by using EEG we addressed whether cortical processing of tactile inputs received at the thumb and index finger tips were related to the touchscreen parameters. We performed multiple regressions across all electrodes and time points between 30 ms pre-stimulation to 190 ms post-stimulation to relate the inter-individual variations in cortical signal amplitudes to the touchscreen parameters. As increased use of a body part is typically associated with larger cortical signals in the somatosensory cortex and we expected the number of touchscreen touches to be proportional to the cortical signal amplitudes[12,21]. Nevertheless there is some empirical evidence of signal attenuation with training[13]. Intuitively, we expected that the fewer the longer gaps in touchscreen use parameterized by the power-law exponent α the larger the cortical signals. Surprisingly, we found that the higher the number of touchscreen touches the smaller the cortical signals between 60-80 ms and then again 90-120 ms after the stimulations (FIG. 14.1). These timings implicate reduced activity in neuronal populations at the pericentral cortical regions, with the first component likely dominated by the primary somatosensory cortex and the second component dominated by the secondary somatosensory cortex[22]. Notably, the second component was associated with α such that the higher the exponent, the larger the cortical signal. This pattern of results show that the different stages of processing in the sensorimotor cortex correlate with distinct aspects of behavior, and well aligned with the general idea that serial processing involves fundamentally distinct computations at each stage[23-25].

The inputs from the adjacent fingertips are integrated at the early stages of cortical processing—in the primary somatosensory cortex. When adjacent fingers are simultaneously stimulated, interactions within the subcortical and cortical structures result in a smaller cortical signal than expected from the linear sum of the isolated stimulations. This can be partly attributed to lateral inhibitory mechanisms. One possibility is that after such spatial integration by early cortical processing the subsequent processing does not correspond to touchscreen behavior. In our data the theoretical sum of the early cortical potentials (under 60 ms) evoked by the simultaneous stimulation of the thumb and index fingertips were a median of 30% (20-38%) smaller in magnitude than the theoretical sum of the isolated stimulation of the same tips (t-test, n=55, p=2.1×$10^{21}$). Nevertheless, the touchscreen correlates in response to the simultaneous inputs followed the same pattern as the isolated inputs (Supplementary figure). This suggests that reducing the activity of neighboring representations in the primary somatosensory cortex through processes such as lateral inhibition does not fundamentally distort how the information flow is related to the touchscreen behavior.

Our experiments found correlative links between the touchscreen behavior and the basic cortical sensorimotor processes evaluated in the lab. At the very least these links provide new grounds to predict human brain functions by using the data seamlessly generated on touchscreen smartphones and vice versa. It is likely that the links themselves are an outcome of one or combination of the following two possibilities. Firstly, it is possible that touchscreen behavior configured the basic processes of the sensorimotor cortex through use-dependent plasticity. For this the plastic mechanisms in the cortex would need to integrate the number of touchscreen touches over a period amidst all the other functions performed by the hand. Furthermore, the mechanisms would need to capture both the more and the less frequent touchscreen intervals to account for the correlations with the power-law exponent. The second possibility is that the basic processing in the sensorimotor cortex varied from person to person and these variations caused the behavioral differences on the touchscreen. Towards this, slight differences in the generation of touchscreen movements by the brain may cascade into how the overall behavior is structured. The increasingly rich behavioral quantification on touchscreen smartphones is expected to help resolve how brain functions are integrated with the complex real world.

Methods

Subjects

A total of 85 individuals were recruited by using campus wide announcements. The announcements were targeted at right-handed healthy individuals. The handedness was further verified by using a questionnaire[31]. Ownership of a non-shared touchscreen smartphone with an android operating system was a pre-requisite for participation. All experimental procedures were approved according to the Swiss Human Research Act by the cantons of Zurich and Vaud. The procedures also conformed to the Helsinki Declaration. The volunteers provided written and informed consent to participate in the study.

Smartphone Data Collection and Analysis

A custom-designed app that could record the touchscreen events with a minimum resolution of 17 ms (limited by the 60 Hz scan rate of the older smartphones, the maximum scan rate encountered was 120 Hz) was installed in each participant. The app posed as a service to gather the timestamps of touchscreen events that were generated when the screen was in an unlocked state. The operation was verified in a subset of phones by using artificially controlled tactile events. The data was stored locally and transmitted by the user at the end of the study via email. One subject was eliminated as the app intermittently crashed after a software update. The smartphone data collection period preceded the reaction time and EEG measures —except in the measures where smartphone data collection was reinstated after the 2-3 months gap. The smartphone data was processed by using MATLAB (MathWorks, USA) to extract the number of touchscreen touches per day, and pre-existing scripts were used to fit the data with a power-law distribution[32].

Reaction Time Measurements and Analysis

Participants were seated upright while they were instructed to fixate on a gray shape on a computer display. A baffle hid the hand during the measurements. Simple reaction times were measured by using a solenoid tactile stimulator mounted on a micro switch such that the user depressed the switch with the thumb to indicate presence of a stimulus at the same thumb tip. The time intervals were measured over 400 trials, and the trials were separated by a normal distribution between 1.5 and 2.5 s from a warning tone. The stimulus lasted for 10 ms and featured a 1.5 mm diameter cylinder that generated a supra-threshold 2 mN pressure on contact (Heijo Research Electronics, UK). As the stimulus resulted in a faint but audible sound we used a white noise mask through the experiment. The maximum response bound was set at 1 s. To digitize the reaction times the voltages associated with the micro switch were recorded via the BrainAmp (Brain Products GmbH, Germany) digital input ports sampled at 1 kHz. From each individual the reaction time median and skew was extracted by using MATLAB. Moreover, we fitted the reaction time distributions by using an ex-Gaussian three parameter fit[33]. All the participants contributed to the reaction time measures, but one participant was eliminated due to a technical malfunction.

EEG Data Acquisition and Analysis

For EEG measurements the same tactile inputs were used as for the reaction time measures. However, the stimuli were presented both at the index finger and thumb tips. Due to the hours of measurements necessary to gather the tactile evoked potential signals by using EEG subjects were instructed to fixate on a computer display running David Attenborough's Africa series; a white noise mask was played to drown the stimuli mixed with the corresponding soundtrack. In one block of 3000 trials, the index finger alone, the thumb alone and both the tips were stimulated in a pseudo-random order with a gap of 0.75 to 1.25 s. In another block of 1000 trials, the thumb-tip was consecutively stimulated with the effective same gap for the thumb as in the first block. A drink break was provided with a gap of 10 minutes and for a maximum of 10 minutes. To record the EEG signals we used 64 electrodes—62 equidistant scalp electrodes and 2 ocular electrodes—against a vertex reference (EasyCap, Germany). The electrode locations were digitized in a 3D nasion-ear coordinate frame (ANT Neuro and Xensor software, Netherlands) for a representative volunteer. The signals were recorded and digitized by using BrainAmp at 1 KHz. By using EEGLAB, a toolbox designed for EEG analysis on MATLAB, we processed the data offline. The data was referenced to the average of all scalp electrodes and band-pass filtered between 1-80 Hz. The data was epoched and further processed by using independent component analysis. Components dominated by eye movements and other measurement artifacts were eliminated with the help of the EEGLAB plug-in SASICA[34]. The data was thresholded at 80 μV to eliminate large signal fluctuations such as in eye blinks. To estimate the extent of suppression we estimated the area occupied by the signal between 30 to 100 ms post stimulation at the electrode with the largest amplitude on the grand-average. Fifty-five of the 85 participants were recruited towards EEG measures, and one participant was eliminated due to excessive blinks in the data.

Correlational Analysis Linking the Smartphone and Lab Measurements

Reaction time data was linked to the touchscreen parameters by using robust—bisquare—multiple linear regression analysis (MATLAB). The level of significance was set at p=0.05. During this analysis we eliminated one participant due to extreme $\tau_{min}$. Using the linear modeling toolbox LIMO EEG we correlated the EEG data to the touchscreen parameters[35]. The correlation coefficients were estimated across all electrodes in the time period of interest. The significance level of the coefficients was corrected for multiple comparison corrections by using 1000 bootstraps and temporal clustering. The extent of suppression estimated from the selected electrode was correlated to the touchscreen parameters by using multiple regression analysis (MATLAB).

REFERENCES

1. Elbert, T., Pantev, C., Wienbruch, C., Rockstroh, B. & Taub, E. Increased cortical representation of the fingers of the left hand in string players. *Science* 270, 305-307 (1995).
2. Hamilton, R. H. & Pascual-Leone, A. Cortical plasticity associated with Braille learning. *Trends Cogn. Sci.* 2, 168-174 (1998).
3. Münte, T. F., Altenmüller, E. & Jäncke, L. The musician's brain as a model of neuroplasticity. *Nat. Rev. Neurosci.* 3, 473-478 (2002).
4. Kleber, B., Veit, R., Birbaumer, N., Gruzelier, J. & Lotze, M. The Brain of Opera Singers: Experience-Dependent Changes in Functional Activation. *Cereb. Cortex* 20, 1144-1152 (2010).
5. Yarrow, K., Brown, P. & Krakauer, J. W. Inside the brain of an elite athlete: the neural processes that support high achievement in sports. *Nat. Rev. Neurosci.* 10, 585-596 (2009).
6. Gindrat, A.-D., Chytiris, M., Balerna, M., Rouiller, E. M. & Ghosh, A. Use-Dependent Cortical Processing from Fingertips in Touchscreen Phone Users. *Curr. Biol.* 25, 109-116 (2015).
7. Vázquez, A. et al. Modeling bursts and heavy tails in human dynamics. *Phys. Rev. E Phys Rev E* 73, 036127 (2006).
8. Barabási, A.-L. The origin of bursts and heavy tails in human dynamics. *Nature* 435, 207-211 (2005).
9. Oliveira, J. G. & Barabási, A.-L. Human dynamics: Darwin and Einstein correspondence patterns. *Nature* 437, 1251-1251 (2005).
10. Jiang, Z.-Q. et al. Calling patterns in human communication dynamics. *Proc. Natl. Acad. Sci. U.S.A* 110, 1600-1605 (2013).
11. Oliveira, J. G. & Vazquez, A. Impact of interactions on human dynamics. *Phys. Stat. Mech. Its Appl.* 388, 187-192 (2009).
12. Collignon, O. & De Volder, A. G. Further Evidence That Congenitally Blind Participants React Faster to Auditory and Tactile Spatial Targets. at <http://www.researchgate.net/profile/Anne_De_Volder/publication/40755921_Further_Evidence_That_Congenitally_Blind_Participants_React_Faster_to_Auditory_and_Tactile_Spatial_Targets/links/02e7e53901b3c9aaea000000.pdf>
13. Spengler, F. et al. Learning transfer and neuronal plasticity in humans trained in tactile discrimination. *Neurosci. Lett.* 232, 151-154 (1997).
14. Donovan, J. J. & Radosevich, D. J. A Meta-Analytic Review of the Distribution of Practice Effect: Now You See It, Now You Don't. (1999). at <http://www2.lio.se/pages/175710/A%20Meta%20Analytic%20Review%20of%20the%20Distribution%20of%20Practice%20effect.pdf>
15. Franklin, J. C. & Brozek, J. The relation between distribution of practice and learning efficiency in psychomotor performance. *J. Exp. Psychol.* 37, 16-24 (1947).
16. Whitley, J. D. Effects of Practice Distribution on Learning a Fine Motor Task. *Res. Q. Am. Assoc. Health Phys. Educ. Recreat.* 41, 576-583 (1970).

17. Lee, T. D. & Genovese, E. D. Distribution of Practice in Motor Skill Acquisition: Different Effects for Discrete and Continuous Tasks. *Res. Q. Exerc. Sport* 60, 59-65 (1989).
18. Ulrich, R., Rinkenauer, G. & Miller, J. Effects of Stimulus Duration and Intensity on Simple Reaction Time and Response Force. at <http://e.guigon.free.fr/rsc/article/UlrichEtA198a.pdf>
19. Wenar, C. Reaction time as a function of manifest anxiety and stimulus intensity. *J. Abnorm. Soc. Psychol.* 49, 335-340 (1954).
20. Tamm, L. et al. Reaction Time Variability in ADHD: A Review. *Neurotherapeutics* 9, 500-508 (2012).
21. Huber, R. et al. Arm immobilization causes cortical plastic changes and locally decreases sleep slow wave activity. *Nat. Neurosci.* 9, 1169-1176 (2006).
22. Allison, T., McCarthy, G. & Wood, C. C. The relationship between human long-latency somatosensory evoked potentials recorded from the cortical surface and from the scalp. *Electroencephalogr. Clin. Neurophysiol. Potentials Sect.* 84, 301-314 (1992).
23. Inui, K., Wang, X., Tamura, Y., Kaneoke, Y. & Kakigi, R. Serial Processing in the Human Somatosensory System. *Cereb. Cortex* 14, 851-857 (2004).
24. Romo, R., Hernández, A., Zainos, A., Lemus, L. & Brody, C. D. Neuronal correlates of decision-making in secondary somatosensory cortex. *Nat. Neurosci.* 5, 1217-1225 (2002).
25. Del Gratta, C. et al. Topographic Organization of the Human Primary and Secondary Somatosensory Cortices: Comparison of fMRI and MEG Findings. *NeuroImage* 17, 1373-1383 (2002).
26. Grill-Spector, K., Henson, R. & Martin, A. Repetition and the brain: neural models of stimulus-specific effects. *Trends Cogn. Sci.* 10, 14-23 (2006).
27. Rioult-Pedotti, M.-S., Friedman, D., Hess, G. & Donoghue, J. P. Strengthening of horizontal cortical connections following skill learning. *Nat. Neurosci.* 1, 231 (1998).
28. Hsieh, C.-L., Shima, F., Tobimatsu, S., Sun, S.-J. & Kato, M. The interaction of the somatosensory evoked potentials to simultaneous finger stimuli in the human central nervous system. A study using direct recordings. *Electroencephalogr. Clin. Neurophysiol. Potentials Sect.* 96, 135-142 (1995).
29. Gandevia, S. C., Burke, D. & McKeon, B. B. Convergence in the somatosensory pathway between cutaneous afferents from the index and middle fingers in man. *Exp. Brain Res.* 50, 415-425 (1983).
30. Forss, N., Jousmäki, V. & Hari, R. Interaction between afferent input from fingers in human somatosensory cortex. *Brain Res.* 685, 68-76 (1995).
31. Oldfield, R. C. The assessment and analysis of handedness: The Edinburgh inventory. *Neuropsychologia* 9, 97-113 (1971).
32. Clauset, A., Shalizi, C. R. & Newman, M. E. Power-law distributions in empirical data. *SIAM Rev.* 51, 661-703 (2009).
33. Lacouture, Y. & Cousineau, D. How to use MATLAB to fit the ex-Gaussian and other probability functions to a distribution of response times. *Tutor. Quant. Methods Psychol.* 4, 35-45 (2008).
34. Chaumon, M., Bishop, D. V. M. & Busch, N. A. A practical guide to the selection of independent components of the electroencephalogram for artifact correction. *J. Neurosci. Methods* doi:10.1016/j.jneumeth.2015.02.025
35. Pernet, C. R., Chauveau, N., Gaspar, C. & Rousselet, G. A. LIMO EEG: A Toolbox for Hierarchical LInear MOdeling of ElectroEncephaloGraphic Data. *Comput. Intell. Neurosci.* 2011, e831409 (2011).

The invention claimed is:

1. Method for predicting a brain activity response following a tactile stimulus of a finger of a person comprising the steps:
   measuring and recording with the personal device a usage data set of the person on a personal device used by said person, wherein the personal device comprises a touch screen and a processor, wherein the processor tracks and records a number of touchscreen events by the person of the personal device per unit of time and/or wherein the processor tracks and records a temporal course of a battery log of the personal device, wherein the number of touchscreen events corresponds to the number of contacts of a finger on the touchscreen of the personal device, wherein the number of touchscreen events and/or the temporal course of a battery log of the personal device are stored in a non-transitory storage medium of the personal device in an associated usage attribute comprised in the usage data set, and wherein attribute data is associated to each of the at least one usage attribute,
   providing a computational inference model generated from a plurality of brain activity data sets and a plurality of usage data sets, wherein each brain activity data set comprises data derived from a previously recorded brain activity response following a tactile stimulus,
   submitting the attribute data of each of the at least one usage attributes to said computational inference model,
   predicting a brain activity response following a tactile stimulus of said person by calculating a plurality of spatiotemporal brain activity response values by applying said computational inference model to the submitted attribute data,
   displaying the predicted brain activity response to the person for feedback on the impact of the use of the personal device on its brain activity.

2. Method according to claim 1, characterized in that the computational inference model is generated by conducting the following steps:
   providing a plurality of said brain activity data sets,
   providing a plurality of said usage data sets, acquired from said person or from a plurality of persons,
   estimating for each usage data set of the plurality of usage data sets the attribute data associated to the at least one usage attribute, yielding for each usage attribute a plurality of attribute data,
   submitting the plurality of brain activity data sets and the plurality of the attribute data to a regression analysis, particularly a multiple linear regression analysis or a machine learning algorithm, wherein said regression analysis determines said computational inference model.

3. Method according to claim 2, characterized in that the regression analysis is a multiple linear regression analysis wherein said regression analysis is designed such that an event-related coefficient for each of the at least one usage attribute is determined, wherein the computational inference model is particularly a function that relates the attribute data associated to the usage attribute by means of the corresponding event-related coefficient to a brain activity response following a tactile stimulus.

4. Method according to claim 1, characterized in that the at least one usage attribute is/are:
- a use per hour of the personal device by the person, particularly within the past ten days,
- an age at which the person first began using the personal device,
- a time elapsed from a peak of battery drain of the personal device by the person to a measurement of brain activity for providing brain activity data,
- a distribution of time intervals between touchscreen events of the personal device, and/or
- a parameter, particularly a power law exponent, of a distribution of time intervals between touchscreen events of the personal device.

5. Method according to claim 1, wherein the computational inference model is a personal inference model, wherein said plurality of brain activity data sets is acquired repeatedly from a person and wherein the plurality of the usage data sets is acquired from the same person.

6. Method according to claim 1, the computational inference model is a computational population inference model, wherein said plurality of brain activity data sets is acquired particularly repeatedly, from a plurality of persons and wherein the plurality of the usage data sets is acquired from the same plurality of persons.

7. Method according to claim 1, wherein the usage data set is provided to the computational inference model comprising a temporal resolution of at least ten minutes, and wherein said usage data set is particularly also acquired from a touch screen log, a keypad log, a data exchange log and/or an accelerometer of the personal device.

8. Method according to claim 1, wherein said personal device is a smart phone, a tablet computer, or an additional sensor linked, in particular by means of bluetooth or a cable, to the smart phone or tablet computer, the additional sensor being in particular comprised in a smartwatch, an exercise band, a headset, a head-mounted display, or a heart rate monitor.

9. Method according to claim 1, wherein the computational inference model is a spatiotemporal scalp map, particularly comprising the same temporal resolution as the brain activity dataset.

10. Method according to claim 1, wherein each of the plurality of brain activity data sets is acquired by an electroencephalography method, a functional magnet resonance imaging method, a positron emission tomography method, a functional near-infrared spectroscopy and/or an electrocorticography method.

11. Method according to claim 1, wherein an indicator, particularly a value is generated, wherein said indicator is related to the estimated brain activity response of said person and wherein said indicator furthermore is related particularly to a previously estimated indicator for the estimated brain activity response of said person or to an average indicator for the estimated brain activity response of said person or a plurality of persons.

12. Method according to claim 1, wherein the predicted brain activity response to a tactile stimulus of said person by said evaluation of said computational inference model is compared to the estimated brain activity response based on a computational inference model that has been updated with at least one brain activity data set that is recorded after said first estimation.

13. Method according to claim 1, wherein
- the usage data set is generated by an interaction of the person with the personal device,
- the usage data set is particularly stored on said personal device,
- the attribute data is extracted from said personal device,
- the attribute data is particularly stored in a usage database,
- the brain activity data set is acquired, and
- the brain activity data set is stored in a brain activity database.

14. The method according to claim 1, wherein the brain activity response is predicted spatiotemporally on a millisecond timescale in form of a brain activity value that is computed for a plurality of locations for at least one time point after from the computational inference model.

15. The method according to claim 1, wherein the feedback on the impact of the use of the personal device on the brain activity of the person comprises a task-related representation for helping a user to alter a device use by self-regulation.

16. Computer program comprising program code, wherein said program code prompts a computer to execute, if the computer program is loaded, installed or executed on the computer the following steps:
- measuring and recording with the personal device a usage data set of the person on a personal device used by said person, wherein the personal device comprises a touch screen and a processor, wherein the processor tracks and records a number of touchscreen events by the person of the personal device per unit of time and/or wherein the processor tracks and records a temporal course of a battery log of the personal device, wherein the number of touchscreen events corresponds to the number of contacts of a finger on the touchscreen of the personal device, wherein the number of touchscreen events and/or the temporal course of a battery log of the personal device are stored in a non-transitory storage medium of the personal device in an associated usage attribute comprised in the usage data set, and wherein attribute data is associated to each of the at least one usage attribute,
- providing a computational inference model generated from a plurality of brain activity data sets and a plurality of usage data sets, wherein each brain activity data set comprises data derived from a previously recorded brain activity response following a tactile stimulus,
- submitting the attribute data of each of the at least one usage attributes to said computational inference model,
- predicting a brain activity response following a tactile stimulus of said person by calculating a plurality of spatiotemporal brain activity response values by applying said computational inference model to the submitted attribute data
- displaying the predicted brain activity response to the person for feedback on the impact of the use of the personal device on its brain activity.

* * * * *